US 8,598,871 B2

(12) United States Patent
Bahn

(10) Patent No.: US 8,598,871 B2
(45) Date of Patent: Dec. 3, 2013

(54) SYSTEM AND METHOD FOR PHASE OFFSET AND TIME DELAY CORRECTION IN MAGNETIC RESONANCE SPECTROSCOPY DATA

(75) Inventor: Mark M Bahn, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 584 days.

(21) Appl. No.: 12/788,057

(22) Filed: May 26, 2010

(65) Prior Publication Data

US 2011/0066025 A1     Mar. 17, 2011

Related U.S. Application Data

(63) Continuation-in-part of application No. PCT/US2008/084896, filed on Nov. 26, 2008.

(60) Provisional application No. 61/004,279, filed on Nov. 26, 2007.

(51) Int. Cl.
*G01V 3/00*     (2006.01)
*G01R 33/46*    (2006.01)

(52) U.S. Cl.
USPC ............ 324/307; 324/309; 324/318; 600/410

(58) Field of Classification Search
USPC ........................... 324/300–322; 600/407–465
See application file for complete search history.

(56) References Cited

U.S. PATENT DOCUMENTS

| 4,876,507 | A | * | 10/1989 | Van Vaals | 324/307 |
| 5,218,299 | A | * | 6/1993 | Dunkel | 324/307 |
| 5,568,400 | A | * | 10/1996 | Stark et al. | 702/85 |
| 5,838,156 | A | * | 11/1998 | Miyabayashi | 324/307 |
| 6,321,107 | B1 | * | 11/2001 | Derbyshire | 600/410 |
| 7,279,892 | B2 | | 10/2007 | Speier et al. | |
| 7,964,842 | B2 | * | 6/2011 | Koster et al. | 250/282 |

OTHER PUBLICATIONS

PCT International Search Report and Written Opinion, PCT/US2008/084896, Jan. 28, 2009.

* cited by examiner

*Primary Examiner* — Melissa Koval
*Assistant Examiner* — Emily Chan
(74) *Attorney, Agent, or Firm* — Quarles & Brady LLP

(57) ABSTRACT

A method is provided for producing, with a magnetic resonance (MR) system, a nuclear magnetic resonance spectrum that has been corrected for errors arising from phase offsets and time shifts in the acquired spectroscopic data. A spectroscopic data set includes temporal information indicative of the underlying phase offsets and time shifts. In general, this temporal information is utilized to correct for errors in the acquired data. As a result, a plurality of acquired spectroscopic data sets are more accurately combined by first individually correcting each spectroscopic data set for such errors. Exemplary sources of the phase offsets and time shifts include the physical separation between a volume of interest and the detectors in the MRI system. Using the temporal information, $T_2$ decay in the produced spectrum is also corrected.

18 Claims, 26 Drawing Sheets

SYSTEM AND METHOD FOR PHASE OFFSET AND TIME DELAY CORRECTION IN MAGNETIC RESONANCE SPECTROSCOPY DATA

CROSS-REFERENCE TO RELATED APPLICATIONS

This application is a continuation-in-part of PCT Application No. PCT/US08/084896, filed Nov. 26, 2008, which claims the benefit of U.S. Provisional Patent Application Ser. No. 61/004,279 filed on Nov. 26, 2007, entitled "System and Method for Phase Offset and Time Delay Correction in Magnetic Resonance Spectroscopy Data," and which is herein incorporated by reference.

BACKGROUND OF THE INVENTION

The field of the invention is systems and methods for magnetic resonance spectroscopy (MRS) and magnetic resonance imaging (MRI). More particularly, the invention relates to systems and methods for correcting spectroscopic data for errors arising from phase offsets and time delays.

When a substance such as human tissue is subjected to a uniform magnetic field (polarizing field $B_0$), the individual magnetic moments of the excited nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MR systems store a library of such pulse sequences that can be prescribed to meet the needs of many different clinical applications. Research MR systems include a library of clinically proven pulse sequences and they also enable the development of new pulse sequences.

Magnetic resonance spectroscopy (MRS) is based on collecting and analyzing a radiofrequency signal that is produced from the relaxation of excited protons or other spin species, including those that are bound to various chemical compounds. As the spin species relax back to their baseline (i.e., lower) energy state, they emit radiofrequency waves that are detected by the MRS system. The amplitude of each detected signal is indicative of the amount of the particular spin species (or chemical compound) present, while the frequency of each signal is indicative of the chemical structure of the spin species (or chemical compound) and its surrounding environment. Initially, these emitted signals are in phase, even if they originate from different chemical compounds. However, because the emitted signals exhibit different frequencies, they rapidly become out of phase with each other.

Furthermore, during the acquisition of data with a magnetic resonance (MR) system, errors arise due to the inexact nature of the electronic equipment, the distance from the volume of interest (VOI) to the detector, differences in the T2 decay times of the different spin species (or chemical compounds), the size of the VOI, and the off-center location of the VOI relative to the MR detector system. For example, a time delay between when a signal begins to be emitted and the time that the electronic equipment begins to detect the signal can be present in the acquired data. These errors are prone to cause differences in the time delay between the excitation of the sample, called the "zero time", and the acquisition of the emitted signal. Therefore, as a result of these errors, each sample of data has a different initial phase offset and time delay. These time and phase differences present problems when averaging data samples from different sets in order to increase signal-to-noise ratio (SNR).

Typically, MRS is used to generate a one-dimensional frequency spectrum representing the presence of certain chemical bonds in the region of interest. In medical diagnosis and treatment, MRS provides a non-invasive means of identifying and quantifying metabolites from a region of interest, often the human brain. By finding the relative spectral amplitudes resulting from frequency components of different molecules, medical professionals can identify chemical species and metabolites indicative of diseases, disorders, and other pathologies such as Alzheimer's disease, cancer, stroke, and the like. In this context, two nuclei are typically of particular interest, $^1H$ and $^{31}P$. Phosphorus-31 ($^{31}P$) MRS is directed to the detection of compounds involved in energy metabolism relating to membrane synthesis and degradation. Metabolites of particular interest in proton MRS studies include glutamate (Glu), glutamine (Gln), choline (Cho), creatine (Cre), N-acetylasparate (NAA), and the inositols (ml and sl). With new contrast agents such as hyperpolarized carbon-13 ($^{13}C$), metabolic processes can be observed in the human body. For example, in the context of cancer detection, the signal contributions from various metabolites can be analyzed in regions of interest. Also, much work has been done in cardiac energetics using $^{31}P$ spectroscopy.

Over the past two decades, many fast MR spectroscopic imaging techniques have been developed; among them, multiple spin-echo acquisition, echo-planar spatial encoding, and spiral readout. Compared to the traditional chemical-shift imaging (CSI) technique, these methods offer 2- to 4-fold accelerations in data acquisition time. By contrast, Proton-Echo-Planar-Spectroscopic-Imaging (PEPSI) can accelerate data acquisition by an order of magnitude using echo-planar readouts to collect spectral and 1-dimensional spatial information. The PEPSI technique has been developed for clinical MR scanners to measure 2D and 3D metabolite distributions in several minutes and with high spatial resolution. Given its benefit of fast acquisition, the PEPSI technique has already been employed in many clinical MRS studies.

In conventional MRS applications, the signal-to-noise ratio (SNR) is rather low in the acquired spectroscopic data. This can be improved, in general, by using larger samples of data; however, often one also wants to compare brain chemicals from two small volumes of interest. As such, the most common approach to increasing the SNR of spectroscopic data is to sample multiple signals within a defined volume of interest. Furthermore, the SNR can be additionally improved by averaging the samples together.

There are commonly two ways of producing spectra from multi-sample data sets. One is to average the time sampled data first and subsequently Fourier transform (FT) the result when applied to a single data set. The other common method is to FT the individual time samples first, followed by taking the FT of the result. Since the FT is linear, both of these methods give the same result; however, because it is easier to add values together than FT, the first method is usually employed, in which averaged time sample data is transformed. A typical procedure is to collect 16 sets of 16 averaged samples for a total of 256 individual samples. Unfortunately, the assumption that such data sets combine by simple averaging is flawed. In general, this is due to two factors.

First, when a spin species is excited and is located at the center of the VOI, the emitted signal is at its maximum and the signals from all the nuclei are in phase. However, there is a delay time between the excitation of the nuclei and the sampling of the first emitted RF wave due to limitations in the electronic circuits. During this delay, the signals from the spin species at different frequencies fall out of phase and no longer add coherently. In addition, the time delay also causes loss of the signal that is emitted during the time period corresponding to the delay. Moreover, the physical distance between the VOI and the detector also results in the signals from different frequencies arriving at the detector with different phases. The duration of time between excitation and acquisition of the first data sample is unknown and can vary between data sets. As a result, the initial phase of each excitation is unknown and varies unpredictably with each excitation. Only at the initial moment of excitation are all of the emitted signals from the spin species in phase. Second, the $T_2$ decay times of the different spin species often differ and their apparent relative concentrations change over time. As a result, each time sample that is acquired has a slightly different starting time and an arbitrary phase. If the phase and starting times could be made to match, then the spectra could be produced without $T_2$ decay and with all the peaks in phase and at their maximal amplitude.

Further difficulties in producing the spectrum from the data include the situation in which the sample that produces the detected RF signal might not be exactly at the isocenter of the detector system. Instead, the sample might be off the plane of the detector, or in the plane but not on the isocenter of the detectors. Additionally, the detector system itself might be out of calibration. Either of these situations could lead to the detection of waves by the real and imaginary channels that are slightly out of the usual 90 degree phase difference relative to each other.

Because the detectors are generally not sitting exactly at their isocenter the emitted RF waves of two different frequencies will, in general, arrive at the detector with a phase shift relative to the other emitted wave. Since the detectors cannot be at the isocenter, there will always be a phase shift of the waves of one frequency relative to others. Immediately after excitation, the waves emitted from the nuclei are all in phase; however, for each excitation-emission event, the initial phase is random and unknown. Moreover, there is often times a slight time delay between exciting the nuclei and detecting the first signal. In this duration of time, rapid $T_2$ decay effects will result in a loss of signal. This time delay is unknown and might not be consistent between different data acquisition events.

SUMMARY OF THE INVENTION

The present invention overcomes the aforementioned drawbacks by providing a method for producing, with a magnetic resonance (MR) system, a nuclear magnetic resonance (NMR) spectrum from a desired chemical species that has been corrected for phase difference and time delay errors. A plurality of spectroscopic data sets are acquired from a volume of interest in a subject. Each of these spectroscopic data sets is a time series that is more than just a set of data samples taken at random or non-ordered times. The spectroscopic data sets include temporal information indicative of phase offsets and time shifts. In general, the present invention provides a method that utilizes this temporal information to correct for errors in the acquired data.

In conventional MR spectroscopic methods, the temporal information contained in each spectroscopic data set is discarded when the data is averaged together, or when the corresponding spectra produced from such data sets are averaged. However, it is an aspect of the present invention to utilize this temporal information to correct not only for data errors arising from time delays and phase offsets, but also from the physical separation between a volume of interest and the MR detector system. Thus, a method is provided by which the combination of a plurality of spectroscopic data becomes more reliable.

One aspect of the present invention provides a method for correcting phase errors and time shifts that result from the physical separation between a volume of interest (VOI) and the MR detector system. Additionally, errors resulting from a volume of interest (VOI) that is off-center relative to the MR detector system can be corrected. Thus, the final spectrum that is produced is substantially similar to a spectrum that would have been produced if the detector and scanners were located substantially at the isocenter of the detector system. In such a situation, the RF waves of all frequencies are treated as having arrived simultaneously and in-phase, at both the real and imaginary channel detectors at time zero, i.e. the time of the maximal amplitude of emission of the chemical species. Accordingly, the RF waves are treated as having been detected before any $T_2$ decay has occurred. The phase of the signal is further adjusted so that the waves are all at their maximal value and these maximal values are transformed into the final spectrum.

Another aspect of the present invention provides a method for calculating time delays and phase offsets in acquired spectroscopic data and, using this information, correcting the data. In this way, reliable averaging of the data can be performed. Accordingly, a large number of data samples can be combined to create a spectrum having an increased signal to noise ratio, since the errors in the data samples tend to cancel while the signals represented in the data add.

Yet another aspect of the present invention provides a method in which the slope and calibration of a spectrum calibration line are used to convert the real and imaginary coordinates into intensities of the spectrum to produce a phase-corrected spectrum. The slope and calibration of the spectrum calibration line can be determined by the previous calibration of a particular scanner, or by the construction of "circle structures" based on the Fourier transforms of data sets that are offset in time.

Yet another aspect of the present invention provides a method in which high resolution spectra are made by further processing of the data by zero padding and/or using mirrored data sets. These techniques result in further improvement in signal to noise ratio.

Yet another aspect of the present invention provides a method for producing a spectrum having significantly reduced noise. Temporal correction factors are determined using one of the methods described above and are applied to the corresponding acquired spectroscopic data set. From this corrected data set, a plurality of corrected, time-shifted spectroscopic data sets are then produced. Using these corrected, time-shifted data sets, a plurality of corresponding corrected, time-shifted spectra are produced. Information in these corrected, time-shifted spectra are used to determine a temporal trend for each spectral frequency, from which a complex magnitude value associated with that spectral frequency is estimated. This complex magnitude value is a sensitive indicator of whether a signal was emitted at the given spectral frequency, and noise is significantly reduced because voxels without significant signal variation are eliminated.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

GENERAL DESCRIPTION OF THE INVENTION

The following definitions and terms are provided to clarify the description of the present invention and to guide those of ordinary skill in the art in the practice of the present invention. As referred to herein, "temporal information" includes information derived from an acquired spectroscopic data set, or plurality thereof, in which this information is indicative of phase and time shifts present in the acquired data. Examples of "temporal information" include the time at which magnetic resonance (MR) signals are emitted from a volume of interest, the time delay between the time at which MR signals are emitted and when they are detected, and the physical separation between the volume of interest and the detector (for example, as related to the aforementioned time delay). It is noted that as referred to herein, spectra are plotted and discussed in terms of a frequency axis as this provides a clearer framework for describing the present invention. It should be appreciated by those skilled in the art that the finished spectra would be converted to the standard parts per million (ppm) units, in which spectra are usually displayed.

Figure 1A:
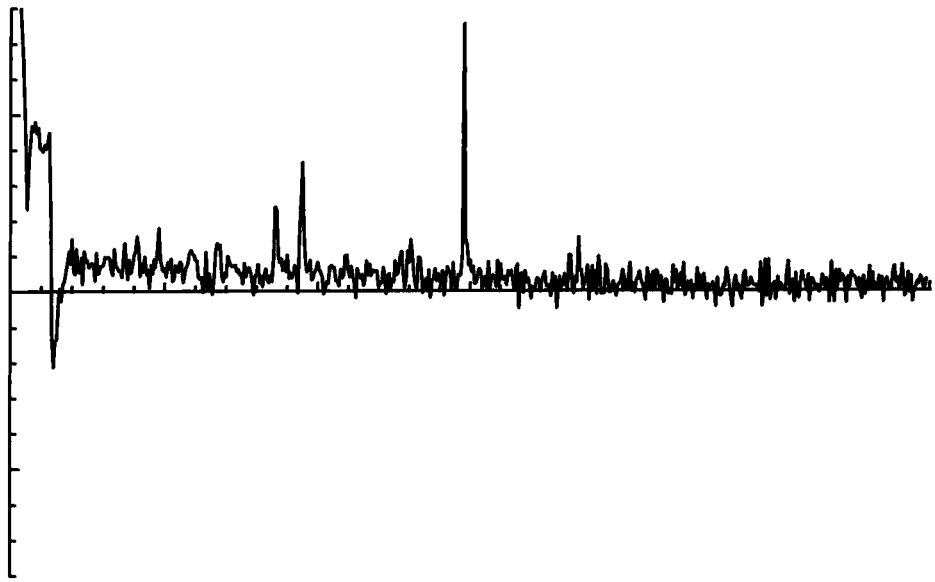
FIG. 1A is an example of a real part of a spectrum produced from a set of acquired spectroscopic data.
Figure 1B:
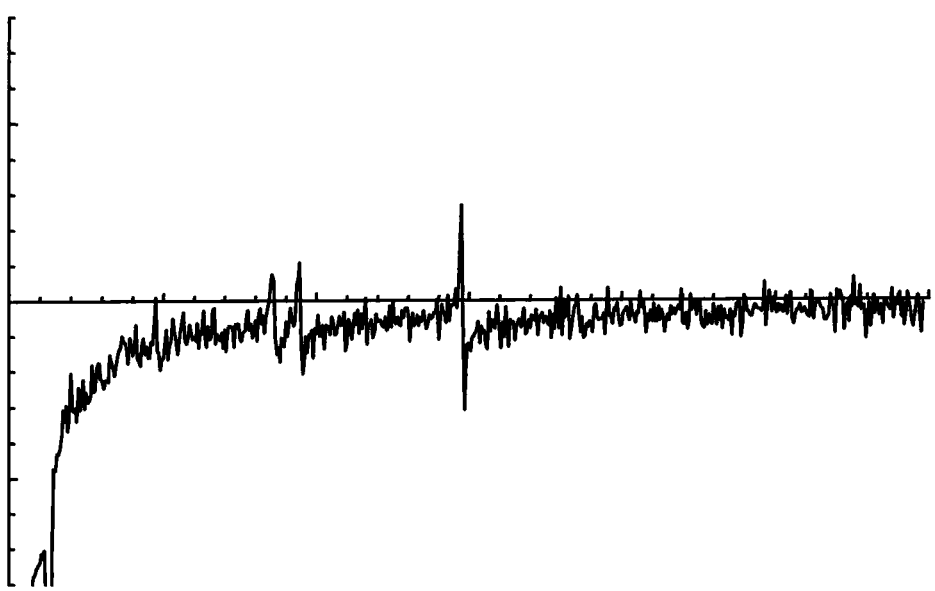
FIG. 1B is an example of an imaginary part of a spectrum produced from the same set of acquired spectroscopic data as FIG. 1A.

In general, magnetic resonance (MR) spectra are nearly symmetrical; however, one end typically has more peaks, and therefore more spectral information, than the other. Accordingly, the two ends of an MR spectrum are referred to as the "spectral end" and the "non-spectral end." Referring particularly to FIG. 1A, the real part of the spectral end of an example MR spectrum is shown. More specifically, only the first 600 points of the spectral end of the spectrum is shown. Similarly, the imaginary part of the first 600 points of the spectral end of the same example spectrum is shown in FIG. 1B. Together, the real and imaginary spectral components give information about the magnitude and phase, respectively, of the different frequencies in the signals received from the VOI. It is noted, however, that some spectra, such as from phosphorus, can have spectral information from some chemical species in the spectral end and some information from other chemical species in the non-spectral end.

Conventional methods for producing MR spectra include acquiring data in the form of RF emissions at fixed intervals of time after the initial excitation of a VOI. This time domain, or spectroscopic, data is then converted to frequency domain data by employing an appropriate Fourier transform. The frequency domain data that is produced corresponds to the emission spectrum at a single time, typically the time of the first RF signal acquisition, or "time one". Using such a method, the real and imaginary parts of the spectrum are typically phased so that the real part has a flat baseline and the imaginary part a non-flat baseline. While this relationship gives good visual appearance of the real spectrum, in the alternative other phase relationships are employed for better calculations and curve fitting. As described above, difficulties arise because the data is not collected starting at zero time, the detector is distant from the sample, and the VOI might not be at the isocenter of the detectors. These factors result in phase dispersion and time shifts in the detected signal, which, in turn, produce errors in the quantification of the spectrum.

Circle Structures

One aspect of the present invention is a method for correcting phase errors in spectroscopic data by employing "circle structures." As referred to herein, a circle structure is a mathematical construct: a parametric plot of the real magnitude of Fourier transformed spectroscopic data, i.e., a spectrum, at each time point versus the imaginary magnitude of the same. The data contained in the circle structure is not just from one time point, but instead is a set of time points. That is to say, for example, the average of the first 20 spectroscopic data sets, then the average of sets 2 through 21, then the average of 3 through 22, and so on. One spectroscopic data set gives one coordinate pair of points in a circle structure for each frequency. After the data points from many spectra are graphed, the circle structures become apparent. Since the time interval between the acquisition of each data set is constant, there is a direct relationship between the phase change and the frequency of the data points in each circle structure. These circle structures are employed to derive additional information about the spectra. More specifically, the circle structure formalism provides a method for correcting for phase errors and time delays in spectroscopic data so that multiple samples can be coherently averaged together prior to Fourier transformation in order to produce a spectrum with increased SNR.

A construction of a circle structure is based on the Fourier transforms of spectroscopic data sets that are offset in time. Consider, for example, the original spectroscopic data set, $\{t_1, t_2, t_3, \ldots, t_n\}$, and its Fourier transform. A second spectroscopic data set can be constructed that has the identical zero time and identical initial phase as the first, but is sampled starting at a time that is one time point later than the original data set. This data set is made, in general, by deleting the first point in the original data set and adding a complex zero at the end of the new data set. Such a process will be described below in more detail.

Figure 2:
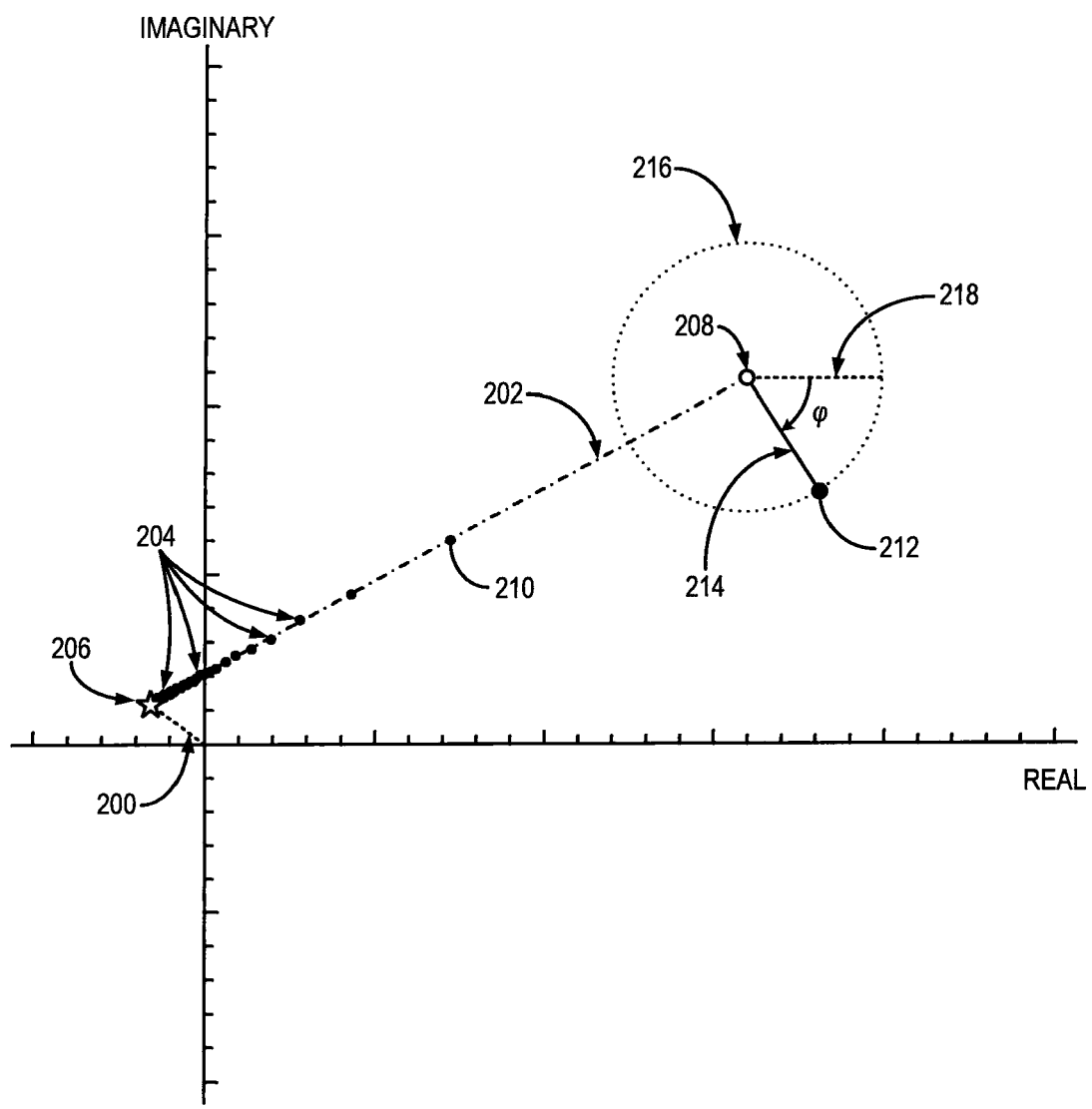
FIG. 2 is a graphic representation of a spectrum reference line and corresponding reciprocal frequency points in accordance with the present invention.

Referring particularly to FIG. 2, a plot indicative of the real and imaginary parts of Fourier transformed spectroscopic data is shown. Here, the horizontal axis corresponds to real valued coordinates, while the vertical axis corresponds to imaginary valued coordinates. The dashed line from the origin, or offset line 200, is proportional to the directional offset of the volume of interest relative to the isocenter of the detectors. In general, the offset line 200 could include a component in a third dimension (e.g., along the z-axis). As will be described in detail below, the spectrum reference line 202 is employed, along with the superimposed reciprocal frequency points 204, to convert the real and imaginary coordinates into the intensity values of the desired MR spectrum. The slope of the spectrum frequency line 202 is related to the phase of the Fourier transform. Accordingly, if the phase of the Fourier transform is zero, the slope of the spectrum reference line 202 will be zero. Likewise, phases of $\pm\pi$ will correspond to slopes of positive or negative infinity, respectively. These phase relationships can be manipulated by multiplying the real and imaginary Fourier transformed data by a unit length complex number. Such a multiplication results in a change of that slope of spectrum reference line 202. This operation is equivalent to a rotation of the coordinate system. The length of this spectrum reference line 202 is indicative of the physical distance between the isocenter of the MR system and its corresponding detectors.

The reciprocal frequency points 204 are points that lie along the spectrum reference line 202. The specific importance of the reciprocal frequency point 204 will be discussed below. The zero point 206 along the line is where the spectrum reference line 202 intercepts the offset line 200 of the VOI. When there is no offset, the zero point 206 of the spectrum reference line 202 is at the origin. The last point, called the scale factor point 208, on the spectrum reference line 202 is a scale factor away from the zero point 206. In particular, the scale factor depends on the distance from the detectors to the isocenter of the system. In general, for a given frequency value of f in the spectrum, the corresponding $f^{th}$ reciprocal frequency point 204 is spaced 1/f away from the zero point 206 towards the scale factor point 208. For example, a second reciprocal frequency point 210 corresponding to the frequency number f=2 is halfway between the zero point 206 and the scale factor point 208. Therefore, the zero point 206 on the spectrum reference line 202 corresponds to the hypothetical frequency number, f=∞.

The spectral point 212 shown on the plot is a data point in the spectrum plotted at its real and imaginary coordinates (i.e., the real and imaginary magnitudes of the spectrum at a given time). The spectral magnitude line 214 is indicative of the magnitude of the spectrum at the corresponding frequency, for this example, the frequency f=1. This information is utilized to make the spectrum. Similarly, the distance between the spectral point corresponding to the spectrum at the frequency f=2 (not shown in FIG. 2) and the second reciprocal frequency point 210 on the spectrum reference line 202 is the magnitude of the spectrum for the spectral frequency f=2. As will be described in detail below, the spectral magnitude line 214 also defines the radius of a circle 216 along which all of the spectral points 212 for a given spectral frequency substantially lie.

The phase angle, φ, of the data point 212 relative to the dashed zero phase line 218 depends on the frequency of the data point 212 and the elapsed time since the true zero time. The phase angle, φ, is measured from the positive real direction and has a value between −π and +π. For example, the positive phase angle, φ, shown in FIG. 2 is measured from the zero phase line 218 in a clockwise direction to the magnitude line 214. The phase angle depends on the time that has elapsed between the true zero time and the time of the data sample that produced the data point at the red dot.

In practice, a circle structure is produced by plotting, for a given frequency value, the real and imaginary magnitudes of the spectrum versus different time points. In order to produce a plurality of spectral values for a given frequency over time, a corresponding plurality of "time-shifted spectroscopic data sets" are first produced from the acquired spectroscopic data. In this way, each spectrum is produced from the same number of time domain data points over the same time interval; however, the first time point in each data set is offset from the first time point in the previous data set. For example, consider the time domain, i.e., spectroscopic, data set:

$\{t_1, t_2, t_3, \ldots, t_n\}$, where $t_n$ is the $n^{th}$ time domain data sample. This first spectroscopic data set is akin to conventional MR spectroscopic data sets. A second "time-shifted spectroscopic data set" can be constructed that has the identical zero time and identical initial phase as the first spectroscopic data set, but is sampled starting at a time that is one time point later than the original data set. Such a data set is produced by deleting the first point in the original data set and adding a complex zero at the end of the new data set. As a result of this process, the spectrum produced from this second spectroscopic data set shows the same magnitudes for each frequency as does the spectrum produced from the first data set, but the phases of the frequency points are offset according to the time interval between the first and second measurement. Accordingly, this second data set has the form:

$\{t_2, t_3, t_4, \ldots, t_n, (0+0i)\}$,

Where (0+0i) is a complex zero. As many as n similar data sets can be made. After that, the data sets would be composed of entirely complex zeros. In actual practice, only about 10 percent of the possible n data sets are produced; however, in the alternative, 2-15 percent of the possible n data sets are produced. When making reference to a specific shifted spectroscopic data set, said shifted data set will herein be referred to by its first time point. For example, the second data set:

$\{t_2, t_3, t_4, \ldots, t_n, (0+0i)\}$,

Will be referred to as the $t_2$-shifted spectroscopic data set, the third data set:

$\{t_3, t_4, t_5, \ldots, t_n, (0+0i), (0+0i)\}$,

Will be referred to as the $t_3$-shifted spectroscopic data set, and so on. For simplicity, the shifted spectra (i.e., the Fourier transform of a shifted spectroscopic data set) corresponding to a shifted spectroscopic data set will similarly be referred to by the first time point. For example, the shifted spectra corresponding to the Fourier transform of the $t_2$-shifted spectroscopic data set will be referred to as the $t_2$-shifted spectrum. Likewise, the non-shifted, original spectroscopic data set may be referred to as the $t_1$ spectroscopic data set and its corresponding Fourier transform, the $t_1$-spectrum.

This method of producing such "time-shifted" spectroscopic data sets is different than collecting a series of data samples at different times and subsequently producing a series of spectra from those separate time series. First, it would be technically different to collect these time series because the delay time between zero time and "time one" is unknown and might be variable. In addition, it is difficult to collect the time series with exactly the right delay relative to other data sets. Most notably, though, the initial phase of each independent data set would differ. On the other hand, producing a plurality of spectroscopic data sets that are each time shifted from the same original spectroscopic data set preserves this phase relationship. Therefore, all of the shifted spectroscopic data sets have the same zero time and the same initial phase. Furthermore, the total magnitude of the spectral signals in the time-shifted spectroscopic data sets is relatively constant because of the short time interval between scans relative to the signal decay time.

In practice N "shifted" spectra are produced from N corresponding time-shifted spectroscopic data sets. As described above, in general, the shifting of the start points of the spectroscopic data is done with the first 2-15 percent of the data. Each produced spectrum has slightly less information than the previous because there is an increasing number of complex zeros at the end of the curve. Therefore, the maximum number of useful spectra that can be produced in this manner is equal to the number of data samples in the original acquired spectroscopic data set, since beyond this the spectra would just be a list of complex zeros.

For each frequency in a given spectrum, the phase of that frequency shifts over time by a fixed amount and at a fixed rate. Since the data points are equally spaced, there is a fixed phase shift between each frequency point in the series of spectra. The amount of change depends on the frequency according to the equation:

$$\Delta\phi = ft^2.$$

Figure 3A:
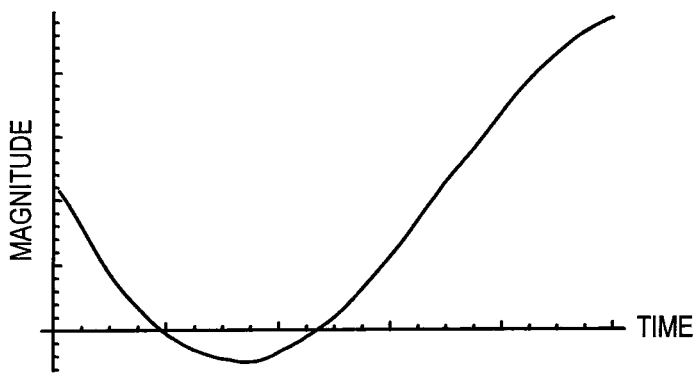
FIG. 3A is an example plot of the imaginary magnitude of a series of time-shifted spectra plotted versus time for a spectral frequency of f=30.
Figure 3B:
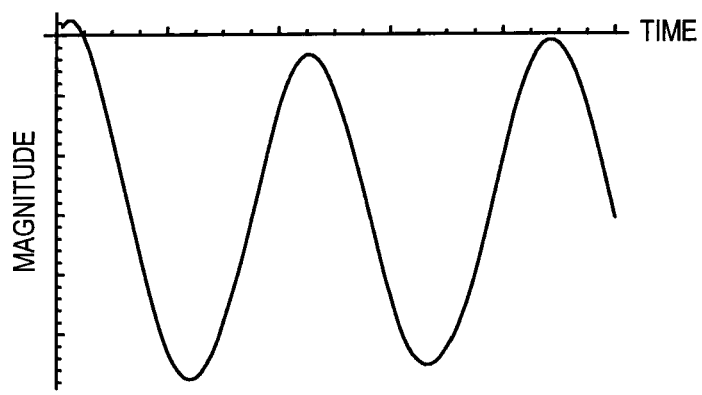
FIG. 3B is an example plot of the imaginary magnitude of a series of time-shifted spectra plotted versus time for a spectral frequency of f=95.
Figure 3C:
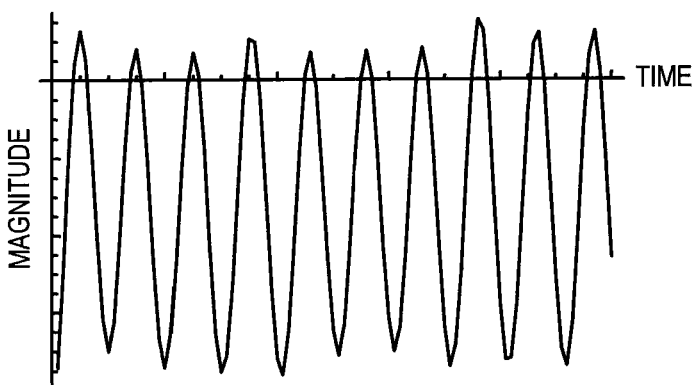
FIG. 3C is an example plot of the imaginary magnitude of a series of time-shifted spectra plotted versus time for a spectral frequency of f=400.
Figure 4A:
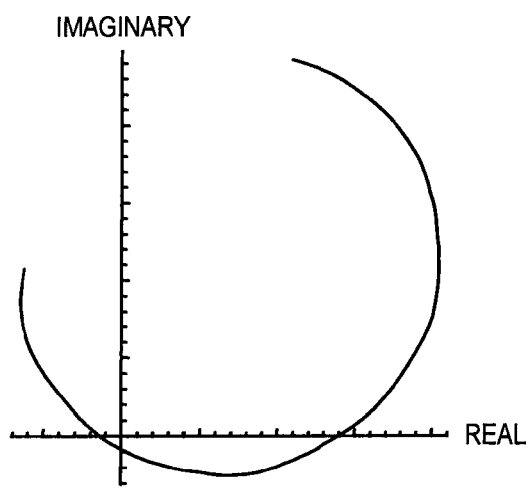
FIG. 4A is an example circle structure produced, in part, from the imaginary magnitudes of the time-shifted spectra represented in FIG. 3A.
Figure 4B:
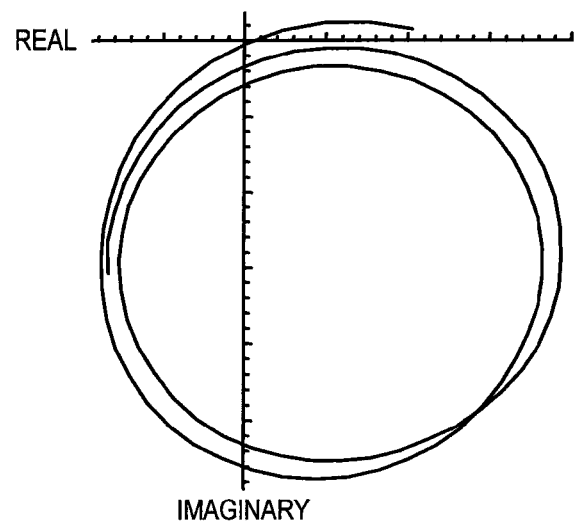
FIG. 4B is an example circle structure produced, in part, from the imaginary magnitudes of the time-shifted spectra represented in FIG. 3B.
Figure 4C:
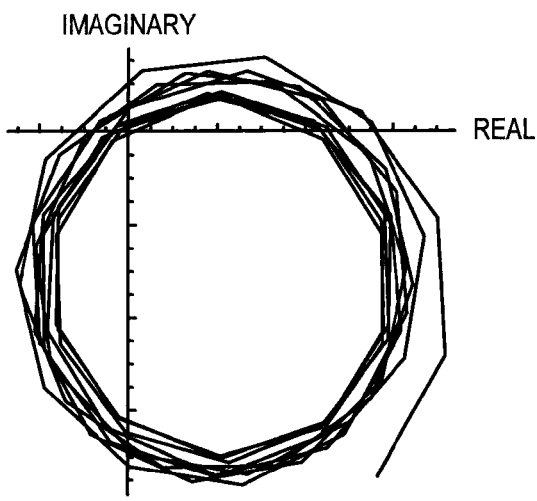
FIG. 4C is an example circle structure produced, in part, from the imaginary magnitudes of the time-shifted spectra represented in FIG. 3C.

This can also be looked at from the perspective of time versus magnitude. In such a way, for each frequency there is the sinusoidal relationship between the magnitude of the spectrum and time. This relationship can be seen, for example, in FIGS. 3A-3C, which show example plots of imaginary magnitude versus time for frequencies of f=30 (FIG. 3A), f=95 (FIG. 3B), and f=400 (FIG. 3C). Circle structures are produced by making a parametric plot of the real magnitude of the spectra at each time versus the imaginary magnitude of the spectra at each time for a given frequency. Using the example plots for the imaginary magnitude of the spectra versus time shown in FIGS. 3A-3C, and the corresponding real magnitude plots (not shown), circle structures are produced. The result of this is shown in FIGS. 4A-4C, in which the imaginary magnitudes are plotted along the vertical (imaginary) axis, and real-valued magnitudes are plotted along the horizontal (real) axis. These plots are nearly circular, and are hence referred to as "circle structures".

Figure 5:
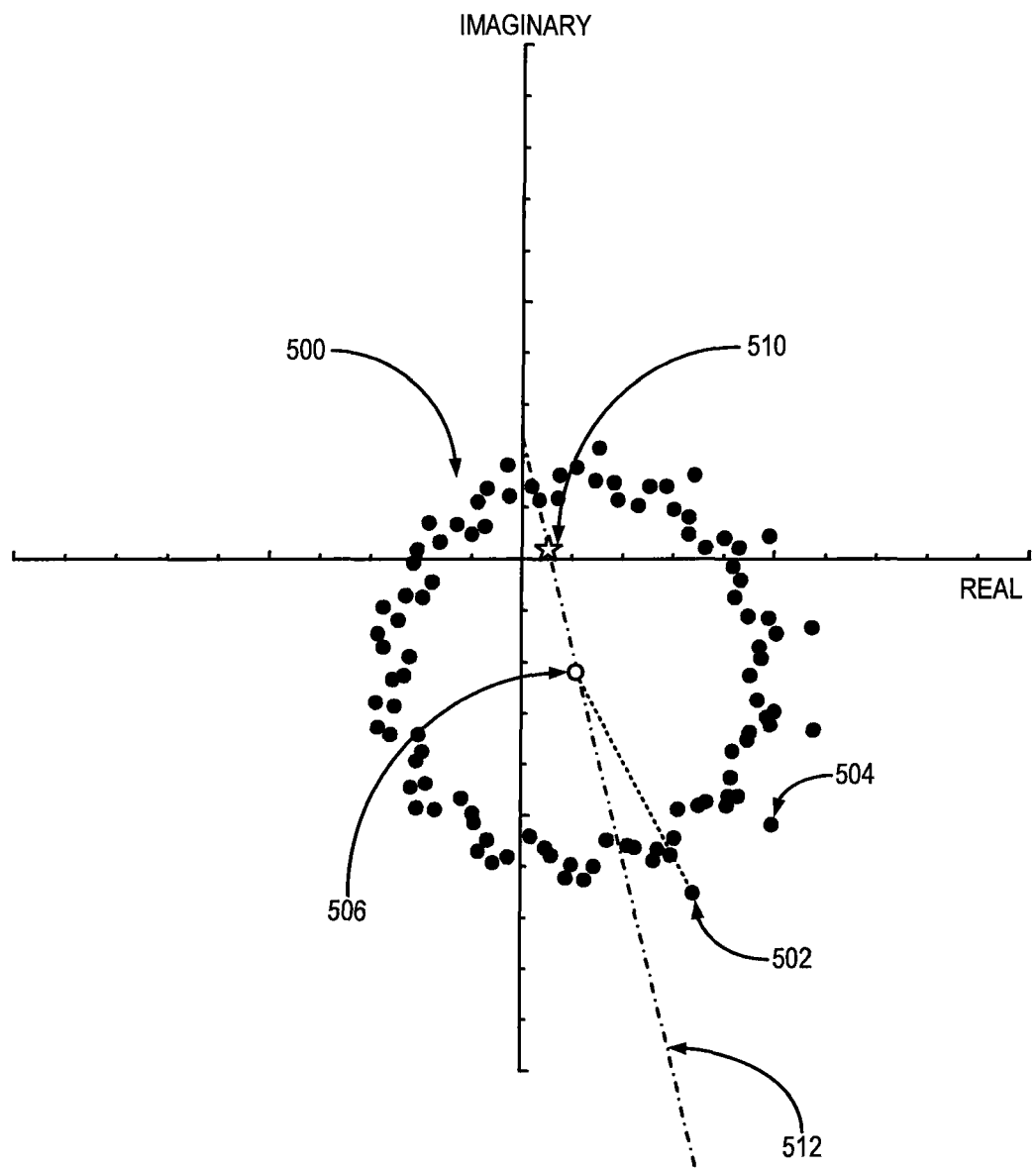
FIG. 5 is an example of a circle structure corresponding to a spectral frequency of f=300.

Referring particularly to FIG. 5, an example of a circle structure 500 is shown corresponding to a spectral frequency of f=300. As with FIGS. 4A-4C, the horizontal and vertical axes represent real and imaginary magnitudes, respectively. In this example, there are 100 points in the circle structure, representing the real and imaginary magnitudes for each spectrum in a series of 100 spectra produced from 100 corresponding time-shifted spectroscopic data sets.

Data points are recorded in a counterclockwise manner beginning from the first data point 502. Accordingly, the first data point 502 represents the point from "time one", the second data point 504 represents "time two", and so on. The center point 506 of the circle structure 500 is indicated by the white point, and is determined by one of several different methods that will be described in detail below. The dashed magnitude line 508 from the center 506 of the circle structure to the first data point 502 represents the phase angle of that point 502. As discussed above, the line of zero phase is along the positive horizontal axis (i.e., the real axis). As time progresses, the points shift counterclockwise. The center 506 of the circle structure 500 is not at the origin. As will be described in detail below, the center 506 of the circle structure provides information that is utilized for correcting time delays and phase errors in the spectroscopic data. The distance from the origin to the zero point 510, indicated by the star, represents the physical distance between the sample VOI and the isocenter of the MR detection system. The center 506 of the circle structure lies along the spectrum reference line 512, as described above. Moreover, the phase angle 514 between the horizontal axis and the spectrum reference line 512 indicates the initial phase of all of the circle structures that correspond to a given spectroscopic data set.

Figure 6:
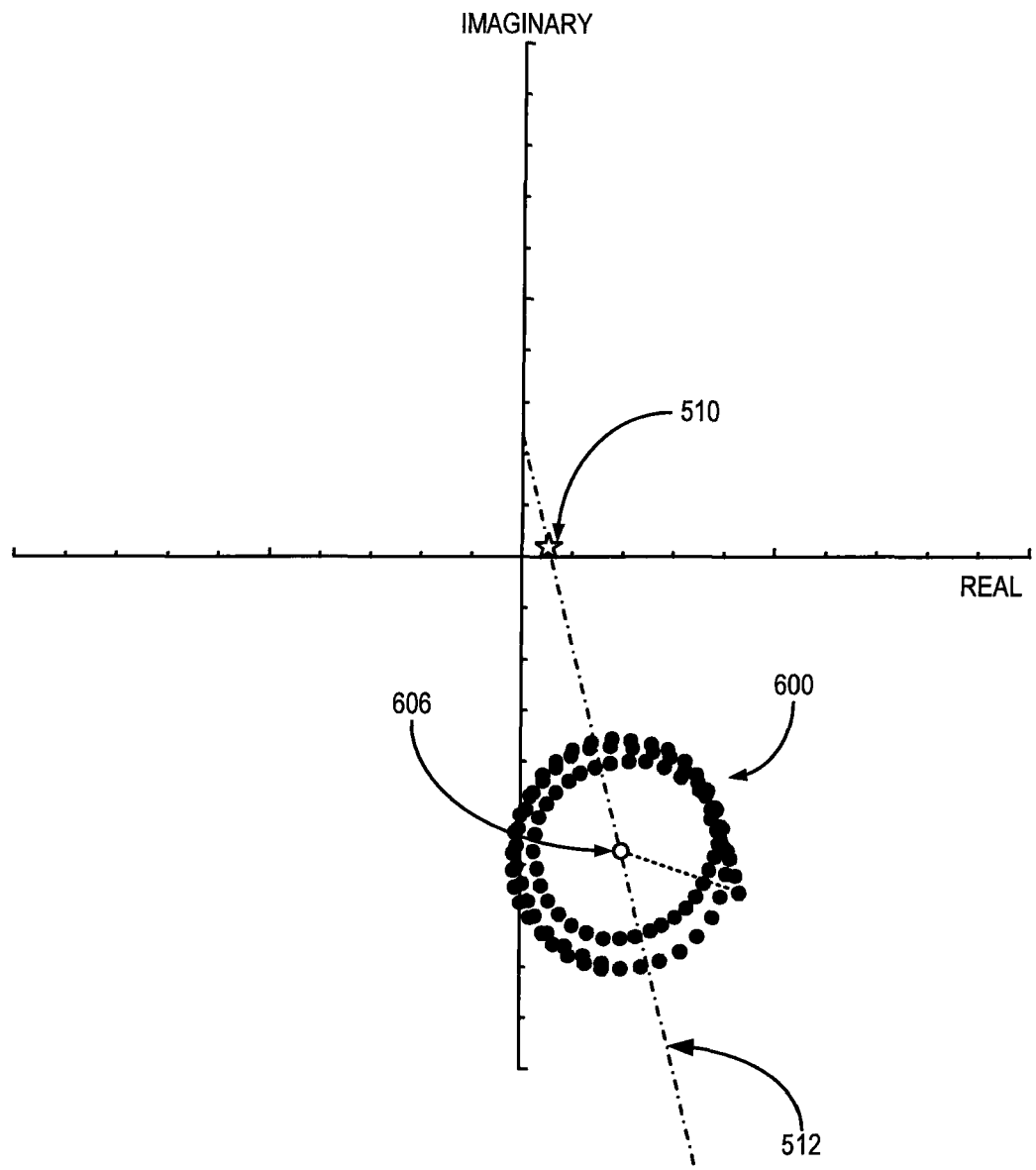
FIG. 6 is an example of a circle structure corresponding to a spectral frequency lower than the circle structure of FIG. 5.

For circle structures corresponding to higher spectral frequencies, the center 506 will be located closer to the zero point 510. In fact, as discussed above, the zero point 510 is indicative of the limiting case for the center of a circle structure 500 that corresponds to a spectral frequency of $f=\infty$. An example of a lower frequency circle structure 600 is shown in FIG. 6. Such a circle structure 600 is produced from the same plurality of shifted spectra as the higher frequency circle structure 500. Note, that the center 606 of the lower frequency circle structure 600 lies along the spectrum reference line 512, just as the center 506 of the higher frequency circle structure 500.

It can be seen from FIGS. 5 and 6 that the distance of the center (506, 606) of each circle structure produced from the same spectra will not necessarily coincide with each other. However, in general, each center (506, 606) will lie along the same spectrum calibration line 512. The location of each center (506, 606) along this line 512 is determined by the distance of the MR system detector to the isocenter of the MR system. Because this distance is not zero, there is a regular and anticipated phase shift of the data, and this distance depends on the spectral frequency. The process of translating the center of a circle structure to the origin is similar to translating the volume of interest (VOI) and the MR system detectors to the origin so that they physically coincide with each other. In this manner, the detected phase of the signals for various frequencies does not change between emission and detection. As a result, it is advantageous to determine the center of the circles structures for a given set of spectroscopic data so that the center of each circle structure can be correspondingly shifted to the origin of the real-imaginary coordinate system.

Estimating the Center of a Circle Structure

In practice, the emitted RF signal from the VOI is sampled periodically. As described above, these sample points define a circle, represented by a circle structure, that surrounds its center. One method for finding the center of a circle structure is to average the coordinates of the points that define the circle. When a sufficiently large number of points evenly surrounds the center a good estimate of the center is produced. However, the circle structures for lower spectral frequencies may not include enough sample points to produce a full circle. This can be seen, for example, in FIG. 4A, which corresponds to an example circle structure for a frequency of $f=30$. In such a situation, the center will be incorrectly estimated toward the side with the data points. Also, for circle structures corresponding to very high spectral frequencies, the period of the sampling may substantially equal the period of the circle. In a situation such as this, the samples might all fall on one side of the circle. A solution to this problem is to determine, based on the sampling frequency and the frequency of each circle, an optimal number of data points to utilize. These data points are then averaged together to give an estimate of the center. It is noted that some circle structures appear more like spirals, while others have constant diameters. This result is from $T_2$ decay. Slow decay results in circle structures having a constant diameter, while fast decay result in more spiral, or helical shaped circle structures.

A secondary correction is possible. For example, when 100 data points are available and the best estimate of the center can be determined by using 70 data points, then the center is estimates based on points $\{1, 2, \ldots 70\}$. Another estimate is then calculated based on points $\{2, 3, \ldots 71\}$, and so on. In this way, 30 estimates of the center point are made. The addition of some of these points might yield better estimates than others. In the end, this process can be stated as a weighted sum of the set of points. The optimal weights are chosen for the estimate of the center of the circle structure, in which some weights might be zero. Alternatively, if the 100 points do not surround the center, a decision can be made to produce more shifted spectroscopic data sets so that a larger number of data points become available for a given frequency.

In addition to averaging the sample points, regression methods can be employed to estimate the center of a circle structure. Such methods incorporate the frequency and number of data points to produce accurate estimates of the center, even if the number of sample points do not result in a complete circle being formed. The estimate of the center of each circle structure determined from the spectra is used in a statistical analysis that simultaneously finds the substantially optimal centers all of the circle structures. The centers of the circles that are difficult to find, for example for low spectral frequencies, are then corrected using the statistical power of the entire set of circle structures.

Translating the Center of a Circle Structure

Another method for determining the center of a circle structure utilizes the real and imaginary components of the spectra for a given frequency plotted versus time. Referring particularly to FIG. 7, a plot of the real magnitude of the spectra versus time, similar to those shown in FIGS. 3A-3C, is shown. The uncorrected plot is shown on the left, where the sinusoidal curve is not symmetrically distributed around the horizontal axis. This indicates that the corresponding circle structure produced from these data points would have a center not located at the origin. By shifting the location of the curve along the vertical axis so that the curve is substantially symmetrically distributed around the horizontal axis, the center of the corresponding circle structure is similarly shifted to the origin.

A decaying exponential function is further incorporated into the model of the sinusoidal signal. For more complicated situations, multiple decaying exponentials can be incorporated into the model. Once the decay parameters for the decay are known, the amplitude at the true zero time can be calculated by extrapolating back based on the knowledge of the interval between the first data point and the true zero time.

Determining the decay parameters allows for corrections of $T_2$ decay effects in the measured spectroscopic data.

Calculating the Location of the Zero Point

Referring again to FIG. 2, the zero point 206 of the spectrum reference line 202 is where the reciprocal frequency point 204 corresponding to a hypothetical infinite frequency lies on the line 202. Put another way, the zero point 206 is the center of a circle structure corresponding to a spectral frequency of f=∞. As discussed above, the zero point 206 can be used to determine the length of the offset line 200 and, thereby, the offset of a VOI from the isocenter of an MR system. In general, the zero point 206 is determined by first producing two separate plots. First, the real magnitude of the center of each circle structure is plotted versus the reciprocal of the spectral frequency corresponding to the circle structure. Accordingly, the second plot includes the imaginary magnitudes of the same plotted versus reciprocal frequency. These two plots are then extrapolated to a reciprocal frequency value of zero. The real and imaginary values associated with this zero crossing identify the zero point 206. It is noted that the zero point 206 might be known based on prior calibrations of the MR system for various off-center volumes of interest; however, if it is not known, one can solve for it as described above.

Demonstration of the Time Between Subsequent Data Samples

With reference still to FIG. 2, the spectrum reference line 202 is employed to correct the phases of the detected RF emission waves by removing the phase offset that results from the physical distance between the detectors and the isocenter of the MR system. This is done by shifting the reciprocal frequency points 204 along the spectrum reference line 202 in proportion to their reciprocal frequency. As noted above, each reciprocal frequency point corresponds to the center of a circle structure produced for the corresponding frequency.

One method for phase error correction includes finding the slope of the spectrum reference line 202. After producing a circle structure for each frequency, the centers of the circle structures are estimated, as described above. The centers of the circles structures (i.e., the reciprocal frequency points 204) lie along the spectrum reference line 202, and thus, can be utilized to determine the slope of the line 202. Using regression techniques, the scales and intervals of the reciprocal frequency points 204 along the spectrum reference line 202 are determined. The zero point 206 can also be estimated in this manner. After determining the scales and intervals for the reciprocal frequency points 204, the points 204 are shifted along the spectrum reference line 202 with their corresponding circle structures. In doing so, the spectral information contained in the circle structures are shifted to new values in the real-imaginary plane. The location of the points and the slope of the spectrum reference line 202 contain the phase and time information. Therefore, phase offsets and time delays are corrected by shifting the line.

Another method for phase error correction includes determining the zero time. First, if the zero time of the system is known, the phase of the data points can be estimated at the time of the first data collection, the scale factor point 208. The phase of the data points can be calculated by determining the best scale factor and best phase value fit to the spectrum reference line and data. This requires very precise knowledge of the zero time. Second, if the zero time is not known, it can be added to the regression equation so that scale, phase, and zero time are all estimated simultaneously in the regression.

The zero time can be determined either before or after translating the center of the circle structures to the origin. Moreover, the zero time is determined from the phase relationships of the circle structures. For a given frequency, the amount that the phase changes in a given time interval is quadratically related by:

$$\Delta\phi = k \cdot f \cdot (\Delta t)^2$$

Where $\Delta\phi$ is the phase shift, f is the spectral frequency, $\Delta t$ is the time interval, and k is a scale factor. Given an initial phase, $\phi_0$, and a zero time equal to zero, the phase after a length of time, $\Delta t$, will be:

$$\phi_0 + k \cdot f (\Delta t)^2 = \phi_0 + f t^2.$$

It is noted that the instantaneous change of phase per time is the linear derivative of the above quantity.

Figure 7A:
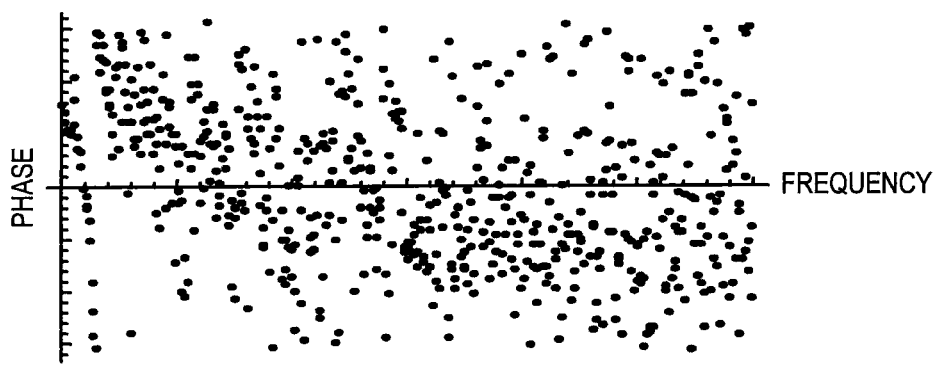
FIG. 7A is an example plot of the phase of spectral data points plotted versus frequency for a given time point.
Figure 7B:
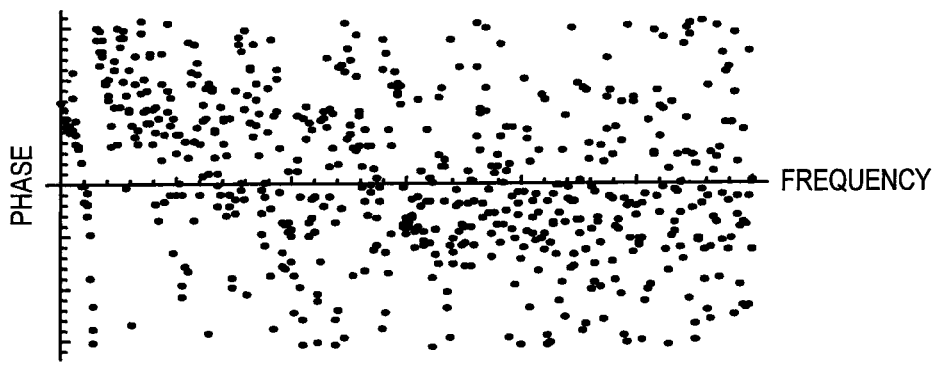
FIG. 7B is another example plot of the phase of spectral data points plotted versus frequency for a different given time point.
Figure 7C:
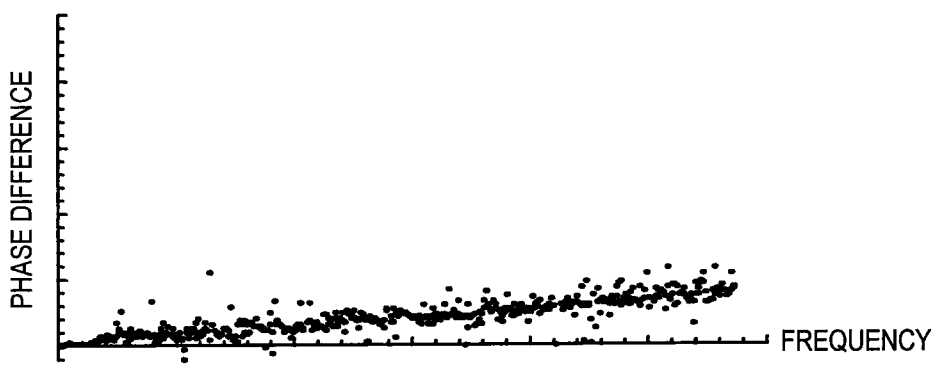
FIG. 7C is a plot of a phase difference line data indicating the phase difference between the plot of FIG. 7A and the plot of FIG. 7B.

A method for determining the zero time is described with reference to FIGS. 7A-7C, 8, and 9 below. First, referring particularly to FIGS. 7A-7C, for each frequency, the difference in phase for two successive points in time is calculated. For example, FIGS. 7A and 7B are a plot of the phase of each data point in a given spectrum (i.e., Fourier transformed shifted spectroscopic data set) versus the spectral frequency of that data point. In this example, FIG. 7A represents the data in an exemplary $t_1$-spectrum and FIG. 7B represents the data in an exemplary $t_2$-shifted spectrum. Accordingly, FIG. 7C represents the phase difference between the $t_2$-shifted spectrum and the $t_1$-spectrum shown in FIGS. 7B and 7A, respectively. In FIG. 7C, it can be seen that the phase difference between two time shifted spectra substantially follows a linear relationship. Therefore, a linear regression can be performed on the phase difference data, such as that plotted in FIG. 7C, to produce a "phase difference line", of which the slope is determined. In general, this linear relationship holds regardless of whether the time points are immediately successive or not. For example, and with reference now to FIG. 8, four different example phase difference lines are shown. These lines indicate the phase difference plotted versus frequency between the $t_1$-spectrum and the $t_2$-shifted spectrum (short dashed line), $t_3$-shifted spectrum (dotted line), $t_4$-shifted spectrum (long dashed line), and $t_5$-shifted spectrum (solid line). Therefore, each of these lines indicate the phase accrual for each spectral frequency in the shifted spectra corresponding to a time difference between an initial measurement.

The slopes of each of these respective lines are then plotted versus the "time difference" that they represent. For example, the phase difference line corresponding to the phase difference between the $t_2$-shifted spectrum and the $t_1$-spectrum indicates a time difference of $\Delta t=1$. Likewise, the phase difference line corresponding to the phase difference between the $t_3$-shifted spectrum and the $t_1$-spectrum indicated a time difference of $\Delta t=2$. In general, the time difference between a spectroscopic data set (or its corresponding spectrum) having an initial time point $t_m$ and a spectroscopic data set having an initial time point $t_m$ is given by:

$$\Delta t = m - n.$$

Figure 8:
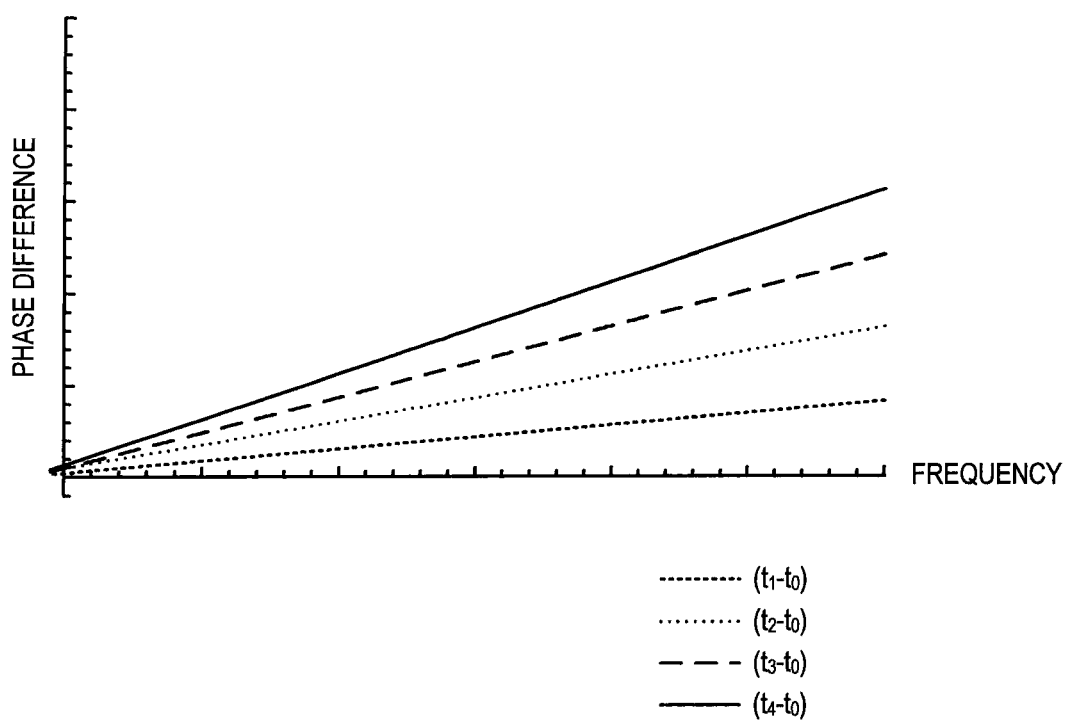
FIG. 8 is plot of four example phase difference lines.
Figure 9:
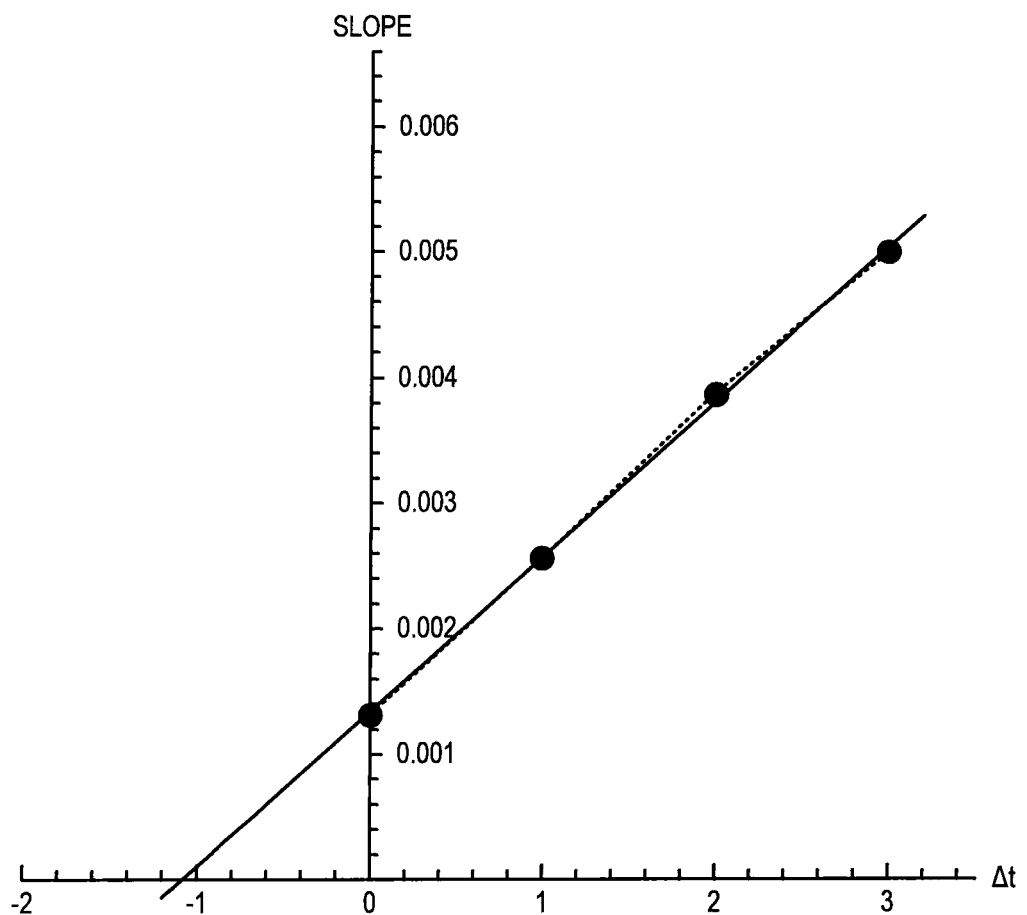
FIG. 9 is a plot of the linear regression of the slopes of the phase difference lines of FIG. 8.
Figure 10:
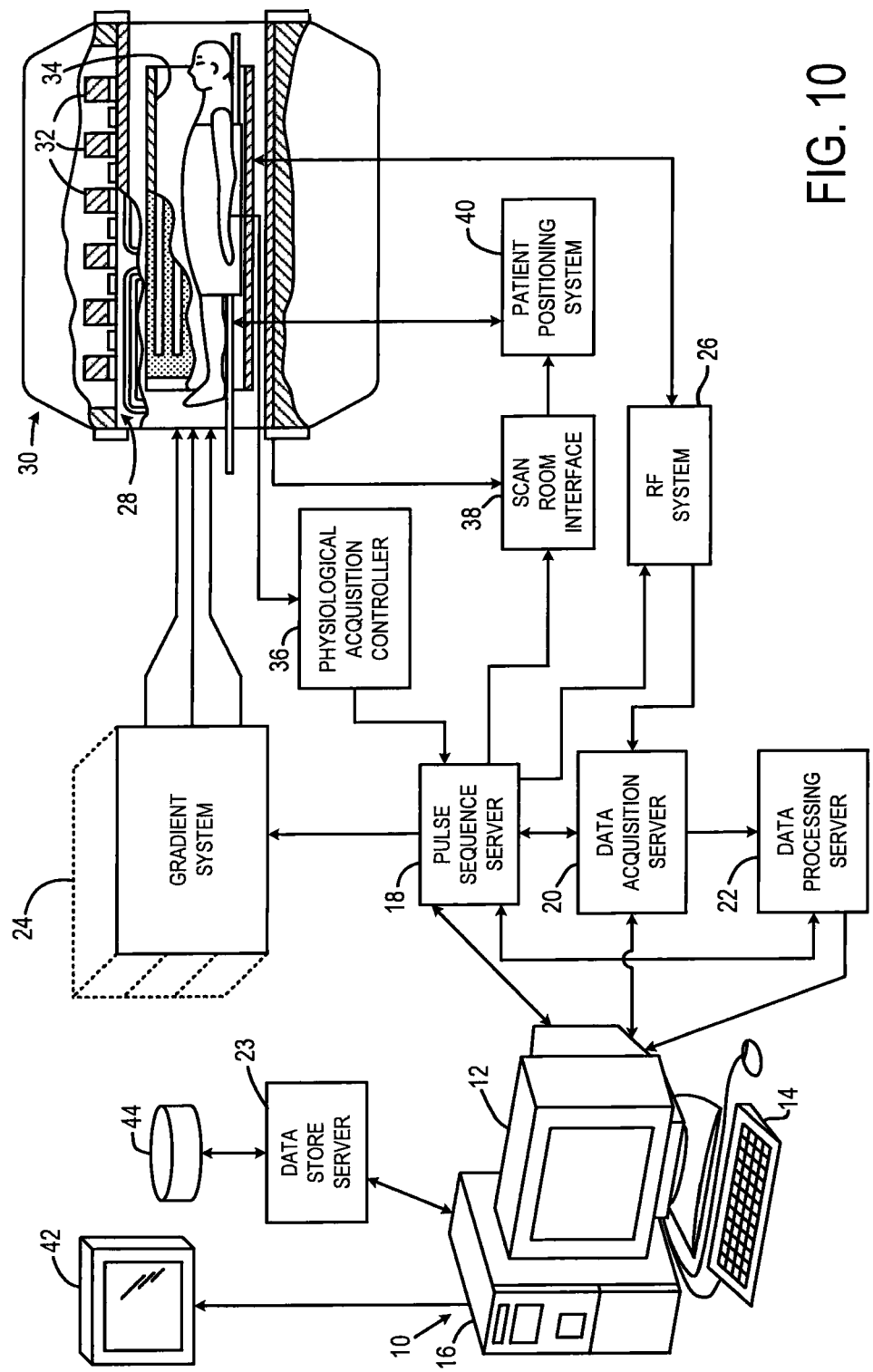
FIG. 10 is a block diagram of an MR system for use with the present invention.

An exemplary plot of the slopes determined from the phase difference lines in FIG. 8 versus the corresponding time difference is shown in FIG. 9. The data points in this plot are fitted using a linear regression method to determine the zero time. While this method for determining the zero time if effective, there is a statistical issue with this approach. The sets of data representing the difference in phase for different time intervals are all derived by subtracting the same data set (phase at time $t_1$) from the other data sets (phase at time $t_2$, $t_3$, $t_4$, and $t_5$). Such a method can introduce a bias in the solution.

The statistics, however, can be improved if the phase versus frequency plots, such as those shown in FIGS. 7A and 7B, are directly fitted. In this method, a quadratic equation is employed when fitting the data. The equation being fitted, therefore, is:

$$A + B \cdot f + C \cdot f^2,$$

Where A, B, and C are parameters determined in the fitting process and f is the spectral frequency. The slope determined by this approach is therefore an instantaneous slope. The fitting equation includes an aliasing term since the data is in aliased form (i.e., lies between $-\pi$ and $+\pi$). Furthermore, instead of fitting each of the data sets separately and somehow combining the fitted values, the data sets are fitted simultaneously to give the optimal parameters. Once the fitted curve is determined, the zero time can be calculated in a similar manner as the one set forth above with respect to the linear regression method.

The methods described above are based on keeping the phase relationship between the real and imaginary components of the shifted spectra fixed. The phases relative to each other are varied by shifting in time, or by calculating the phases based on knowledge of zero time. In addition the phases relative to each other can be varied by estimating the phases based on their predictable regularity to each other and to the corresponding distances along the spectrum reference line 202. The positions of the spectral data points 212 are moved in a known way so that some or all of the following can be calculated: the slope of the spectrum reference line 202, the scale factor point 208, the zero point 206, the position of the reciprocal frequency points 204 on the line, and the length of the magnitude line 214.

Non-Spectral End

The circle structure formalism described in detail above can be generalized and employed to correct spectroscopic without producing shifted spectroscopic data sets and circle structures therefrom. Therefore, a corrected spectrum can be generated from the Fourier transform of the time domain, or spectroscopic, data without going through the actual step of creating circle structures. However, as will be described below, utilizing aspects of the circle structures approach can have additional benefits. As described above, the circle structure method was used primarily to construct a spectrum reference line and to determine and scale reciprocal frequency points (that is, center points of the circle structures) along said line. The following method is based on the circle structure formalism and will be described using the circle structure ideas.

As detailed above, the basis of the circle structure method is that the value of the Fourier transform of a spectroscopic data set for a given spectral frequency can be viewed as a point on the radius of a circle structure. The center of such a circle structure is not immediately known; however, an estimate is readily calculated. Accordingly, it was discussed above that the center of each circle structure is located substantially at the corresponding reciprocal frequency point on a line in the real-imaginary plane, referred to as the spectrum reference line.

Moreover, there is a point on the spectrum reference line that corresponds to where a circle structure representative of data corresponding to an infinite spectral frequency would lie. The data for a given frequency f lies along the spectrum reference line centered at a scale factor times 1/f away from the zero point, which corresponds to the reciprocal frequency point for $f=\infty$. The distance between the data point in the real-imaginary plane and the corresponding reciprocal frequency point indicated the spectral value for that frequency.

Looking at the Fourier transform of a spectroscopic data set, it can be seen that one end has peaks corresponding to the spectrum, while the other end does not and will accordingly be referred to as the "non-spectral end". This non-spectral end can be thought of as a baseline curve with a spectrum of zero magnitude superimposed. Thus, the non-spectral end of the curve is equivalent to the spectrum reference line and the spectral end is used to produce the spectrum. The single point in the spectral end at each frequency can be thought of as a single radius point in the corresponding circle structure. Therefore, the radius of the circle structure is calculated as the distance of this single point to the spectrum reference line, or in this case, the point in the non-spectral end at the corresponding frequency.

As with the presentation of the circle structures, each point of spectral data is plotted as a point in the real-imaginary plane. The spectrum reference line is derived by fitting the plot of the spectral data versus reciprocal frequency. Here the real and imaginary parts are fitted separately; however, they could be fitted simultaneously as well. The zero intercept of the fitted data is the extrapolation of the spectral data to the hypothetical infinite frequency. As described above, this hypothetical infinite frequency corresponds to a reciprocal frequency point called the zero point. This zero point is indicative of the offset of a VOI from the isocenter of an MR system.

To determine the magnitude of the spectrum at a given spectral frequency, the radius of the circle structure corresponding to that spectral frequency is determined. As mentioned above, the center of a circle structure corresponds to the point on the fitted line corresponding to the reciprocal frequency. These points are located along the fitted line at:

$$(0+0i) + \alpha \cdot u,$$

Where $(0+0i)$ is a complex zero, $\alpha$ is a distance scale factor, and u is a unit vector that lies along the fitted line. The distance is just the length of the vector resulting from subtracting the point on the line from the spectral data point.

In another method, the distance scale factor can be incorporated in the fitting process. The values of the spectra at various frequencies in the non-spectral end correspond to a mirror image of frequencies on the spectral end; however, the non-spectral end includes spectrum values of zero. Thus the non-spectral end can be employed to produce the spectrum reference line 202 by plotting the spectrum values versus:

$$\alpha, \frac{\alpha}{2}, \frac{\alpha}{3}, \ldots, \frac{\alpha}{n},$$

Where $\alpha$ is the distance scale factor.

Mirrored Spectroscopic Data Sets

An assumption of the Fourier transform is that the function being transformed is periodic. Another assumption is that the data is smooth, or put another way, the data is assumed to be continuous. Along the same line of reasoning, it is beneficial if the data also has a continuous derivative. One way to satisfy these periodicity and continuity assumptions is to multiply the original data with functions that smoothly go to zero over a relatively short time interval. This leads to data that smoothly starts from and ends at zero. In such a manner, the data becomes periodic, albeit with a substantially infinite period, and is smooth.

Applying such a method works well for the tail end of the data (that is, the late time points) because they are already at or near zero due to the natural time decay of the data. However, at the beginning of the curve there is more pertinent spectral information included in the first few time points. This information is altered and possibly lost or distorted if the beginning points are forced to go smoothly to zero. Therefore, another approach to improving data to match the mathematical assumptions of the Fourier transform is to reverse the order of the data and create a new data set that is twice as long by concatenating the reversed data in front of the original data. Such a data set is herein referred to as a mirrored data set.

The beginning and end of these mirrored data sets can be smoothly taken to zero without loss of pertinent spectral information. It should be noted that the middle point where the two datasets are placed back to back does not have a smooth derivative; however, this is a minor problem for the Fourier transform compared to having both a large discontinuity and a discontinuous derivative.

The circle structures produced from a mirrored data set exhibit a unique property. Specifically, the line determined by the centers of the circle structures is the origin of the real-imaginary plane. Therefore, as a result of the symmetric nature of the mirrored data set, the circle structures are automatically centered on the origin. Moreover, the circle structures produced in such a manner are more circular than the circle structures produced using the method described above in detail. As a result, the magnitudes of the circle structures can be accurately calculated by finding the mean of their magnitudes. Therefore, radii of each circle structure can be accurately measured using a single data point. By using the first spectrum in the series of shifted spectra one can accurately estimate all of the radii, thus the shifted spectroscopic data sets and their corresponding shifted spectra need not be produced. This method provides the estimation of the spectra at a resolution of twice the original resolution (for example, 1200 points instead of 600) by using the spectra produced from the mirrored data set. Such a method provides a substantial saving of time and reduction of computational burden. In addition, a mirrored data set can be combined with zero padding to produce an increased resolution. As an alternative method, after the true zero time is known the time points in the original spectroscopic data set can first be extrapolated to zero, after which, the spectroscopic data set can be mirrored and the respective spectra found.

Although the spectrum produced in the foregoing manner resembles a true spectrum, the relative amplitudes of the spectral peaks are not correct. The greatest difference between the spectrum from a mirrored data set versus a non-mirrored data set is that the noise baseline is incorrect. However, regression methods are used to create a function that maps the values from the mirrored data spectrum into a spectrum with correct relative peak values. This calibration step utilizes a standard spectrum to which the mirrored spectrum is fitted. An exemplary calibration factor, K(f), has the following form:

$$K(f)=A+B \cdot f+C \cdot m(f)+D \cdot m(f)^2+E \cdot m((f))^2+F \cdot \log(m(f)),$$

where m(f) is the spectrum produced from the mirrored data set. The coefficients A, B, C, D, E, and F are fitted using a nonlinear regression method to the standard spectrum.

In the alternative, a different calibration is performed, in which the original spectroscopic data is phase shifted so that the corresponding spectrum reference line has a slope of m=0. This phase shifted data is then mirrored as described above and Fourier transformed to produce a spectrum. Since the slope of the reference line is zero in this case, the reflection retains the same slope. A different offset is fitted so that the spectrum from the original data and the spectrum from the reflected data are nearly identical as shown below.

Enhanced Magnetic Resonance Spectroscopy Resolution

As a result of the increased SNR and reliability when averaging data sets together, high resolution images can be made by zero padding of the spectroscopic data sets. For example, if the original data set had 4096 complex elements, the end of this data set can be padded with 31 sets of 4096 complex zeros. Such an example produces a data set with 39 times the original number of elements. Because of memory constraints resulting from computer hardware; however, an entire such data set might not be able to be processed at one time. Therefore, a single, smaller region of the spectrum is specified for processing. This method is herein referred to as the magnetic resonance spectroscopy (MRS) microscope, since the method effectively "zooms in on" a portion of the spectrum for a closer look.

The spectral peaks are enhanced by subtracting the background from each data set before averaging them together. The background is selected as the minimum value over the range. As a result of this process, the data sets that are produced no longer contain quantitative information; however, this method is useful for qualitatively locating peaks of interest. For example, if a peak at a particular location is of particular interest, the individual data sets are normalized to the peak value at that location before averaging them. This accentuates the peak of interest because it is now substantially "noise free".

DETAILED DESCRIPTION OF THE INVENTION

Referring particularly to FIG. 1, the preferred embodiment of the invention is employed in an MRI system. The MRI system includes a workstation 10 having a display 12 and a keyboard 14. The workstation 10 includes a processor 16 that is a commercially available programmable machine running a commercially available operating system. The workstation 10 provides the operator interface that enables scan prescriptions to be entered into the MRI system. The workstation 10 is coupled to four servers: a pulse sequence server 18; a data acquisition server 20; a data processing server 22, and a data store server 23. The workstation 10 and each server 18, 20, 22 and 23 are connected to communicate with each other.

The pulse sequence server 18 functions in response to instructions downloaded from the workstation 10 to operate a gradient system 24 and an RF system 26. Gradient waveforms necessary to perform the prescribed scan are produced and applied to the gradient system 24 that excites gradient coils in an assembly 28 to produce the magnetic field gradients $G_x$, $G_y$ and $G_z$ used for position encoding MR signals. The gradient coil assembly 28 forms part of a magnet assembly 30 that includes a polarizing magnet 32 and a whole-body RF coil 34.

RF excitation waveforms are applied to the RF coil 34 by the RF system 26 to perform the prescribed magnetic resonance pulse sequence. Responsive MR signals detected by the RF coil 34 or a separate local coil (not shown in FIG. 1) are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays (not shown in FIG. 1).

The RF system 26 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2},$$

and the phase of the received MR signal may also be determined:

$$\phi = \tan^{-1}\left(\frac{Q}{I}\right).$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 that receives signals from various sensors associated with the condition of the patient and the magnet system. It is also through the scan room interface circuit 38 that a patient positioning system 40 receives commands to move the patient to desired positions during the scan.

The digitized MR signal samples produced by the RF system 26 are received by the data acquisition server 20. The data acquisition server 20 operates in response to instructions downloaded from the workstation 10 to receive the real-time MR data and provide buffer storage such that no data is lost by data overrun. In some scans the data acquisition server 20 does little more than pass the acquired MR data to the data processor server 22. However, in scans that require information derived from acquired MR data to control the further performance of the scan, the data acquisition server 20 is programmed to produce such information and convey it to the pulse sequence server 18. For example, during prescans MR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process MR signals used to detect the arrival of contrast agent in an MRA scan. In all these examples the data acquisition server 20 acquires MR data and processes it in real-time to produce information that is used to control the scan.

The data processing server 22 receives MR data from the data acquisition server 20 and processes it in accordance with instructions downloaded from the workstation 10. Such processing may include, for example: Fourier transformation of raw k-space MR data to produce two or three-dimensional images, or MR spectra; the application of filters to a reconstructed image; the performance of a backprojection image reconstruction of acquired MR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display 42 that is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Method for General Corrections

Figure 11:
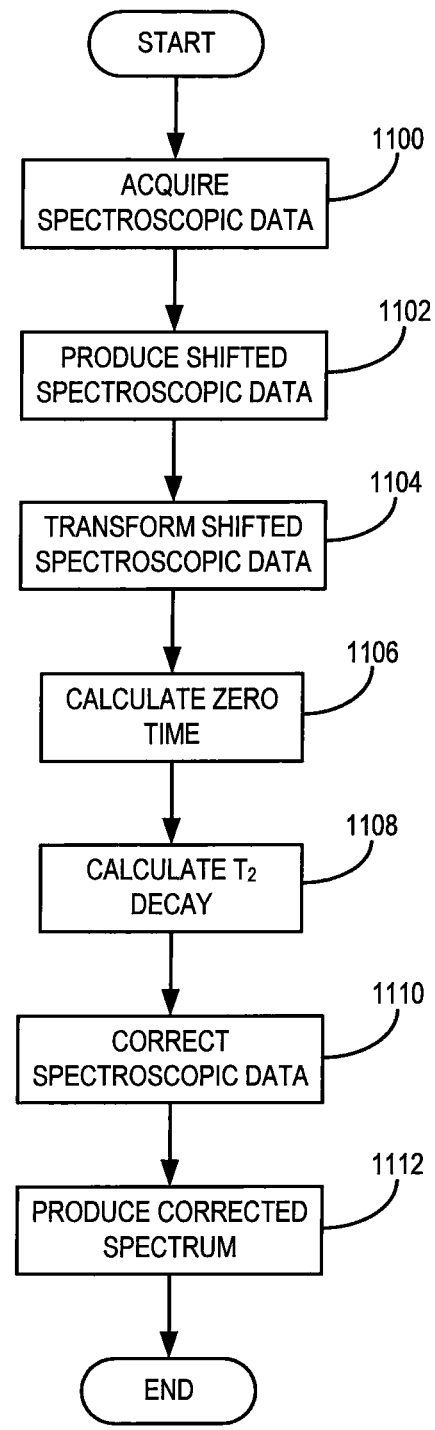
FIG. 11 is a flowchart setting forth the steps of a method for producing a corrected spectrum, using the MR system of FIG. 10, in accordance with one embodiment of the present invention.

Referring particularly to FIG. 11, a method for producing a corrected spectrum begins by acquiring spectroscopic data with an MR system, as indicated in step 1100. In general, the spectroscopic data is acquired with any number of methods known to those skilled in the art. For example, when acquiring spectroscopic imaging data from a subject in an MRI system, a chemical shift imaging (CSI) pulse sequence can be employed to acquire the requisite data. As described above, the spectroscopic data includes information indicative of radiofrequency signals emitted from a volume-of-interest (VOI) in a subject. The first few data points acquired with the MR system are sometimes not accurate, thus the MR system might need to acquire approximately 10 data points before it reaches a reliable equilibrium steady state for data acquisition.

Next, a plurality of shifted spectroscopic data sets are produced from the acquired spectroscopic data, as indicated at step 1102. As described above, these plurality of shifted spectroscopic data sets are produced from the acquired spectroscopic data by removing the leading time point in the data and adding a complex zero to the end of the data in order to preserve the length of the data set. These shifted spectroscopic data sets are then Fourier transformed to produce a corresponding plurality of shifted spectra, as indicated in step 1104.

From the plurality of shifted spectra, the "zero time" is calculated in step 1106. As described above, the zero time indicates the point in time at which the spin species in the VOI are excited with the MR system. The zero time is calculated, for example, by plotting the phase of each data point in a given shifted spectrum (i.e., Fourier transformed shifted spectroscopic data set) versus the spectral frequency of that data point. Each plot produced in this manner is subsequently fitted to a quadratic equation to determine the slope of the fit. Subsequently, the slope corresponding to each shifted spectrum is plotted versus the "time difference" that they represent. For example, the phase difference line corresponding to the phase difference between the $t_2$-shifted spectrum and the $t_1$-spectrum indicates a time difference of $\Delta t=1$. The data points in this plot of slope versus time difference is then fitted using a linear regression method to determine the zero time.

As indicated in step 1108, the $T_2$ decay of the emitted signals is calculated next. This is achieved, for example, by fitting the radius of the circle structure over time to an exponential curve. Once the decay parameters for the decay are known, the amplitude at the zero time can be calculated by extrapolating back based on the knowledge of the interval between the first data point and the zero time. These decay parameters are employed to correct $T_2$ decay effects in the measured spectroscopic data, as indicated at step 1110.

From the $T_2$ decay corrected spectroscopic data, a spectrum indicative of the spin species present in the subject is produced, as indicated at step 1112. This is done by Fourier transforming the spectroscopic data. However, in the alternative, the data is further processed to correct for phase errors.

Phase Error Correction Utilizing a Circle Structure Method

Figure 12:
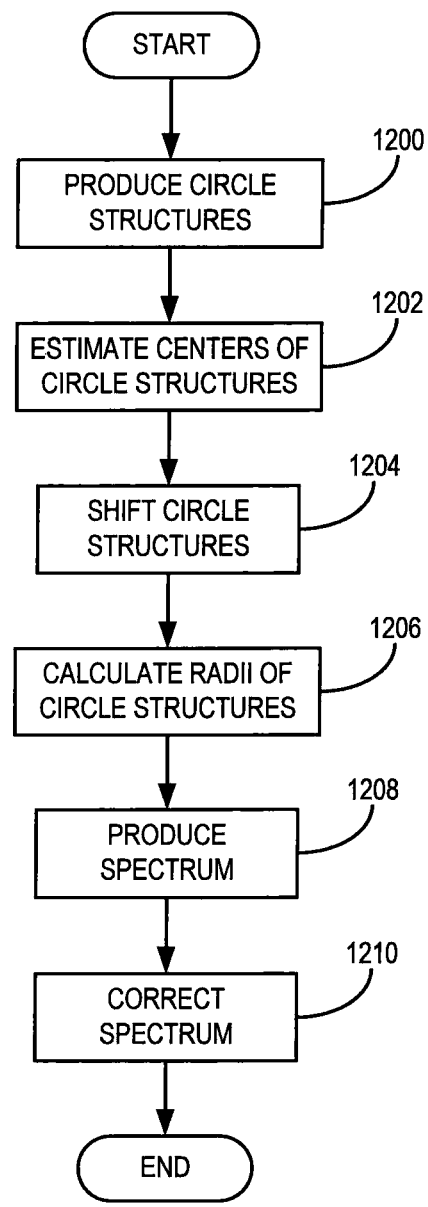
FIG. 12 is a flowchart setting forth the steps of a method for correcting a spectrum, using the MR system of FIG. 10, in accordance with one embodiment of the present invention.

Referring particularly now to FIG. 12, one method for correcting the spectroscopic data for time delays and phase errors begins by, using the plurality of shifted spectra produced in step 1104, producing a circle structure for each spectral frequency, as indicated at step 1200. The details of this method are described above; however, in general, the real and imaginary components of the data points in each shifted spectra that correspond to a given spectral frequency are each plotted in a parametric manner versus time. In doing so, a substantially circular distribution of these data points is produced in the complex (that is, real versus imaginary) plane. The center of each circle structure is subsequently estimated in step 1202. One method in which this is achieved is to average all of the spectral data points in a given circle structure together, as described above. In the alternative, however, regression techniques can be employed to determine the center of a given circle structure.

After the center of a given circle structure has been estimated, the location of that circle structure is shifted to the origin of the complex plane, as indicated at step 1204. The same translation is applied to each point in the circle structure so that the entire circle structure is effectively shifted so that it is centered on the origin. The radius of the circle structure indicates the magnitude of the spectrum for the corresponding spectral frequency. Thus, the radii of each circle structure is calculated in step 1206. As described above in detail, this is achieved by averaging the distance of each data point in a given circle structure from the origin. In the alternative, however, the mean, minimum, or maximum distance of the data points in a given circle structure from the origin can also be utilized. Because the radii of the circle structures are indicative of the magnitude of the spectrum at the respective spectral frequencies, a complete spectrum is produced at step 1208. Finally, as indicated in step 1210, the amplitudes of the produced spectrum are adjusted in accordance with the calculated $T_2$ decay and zero time, as described above in detail.

Phase Error Correction Utilizing a Non-Spectral End Method

Figure 13:
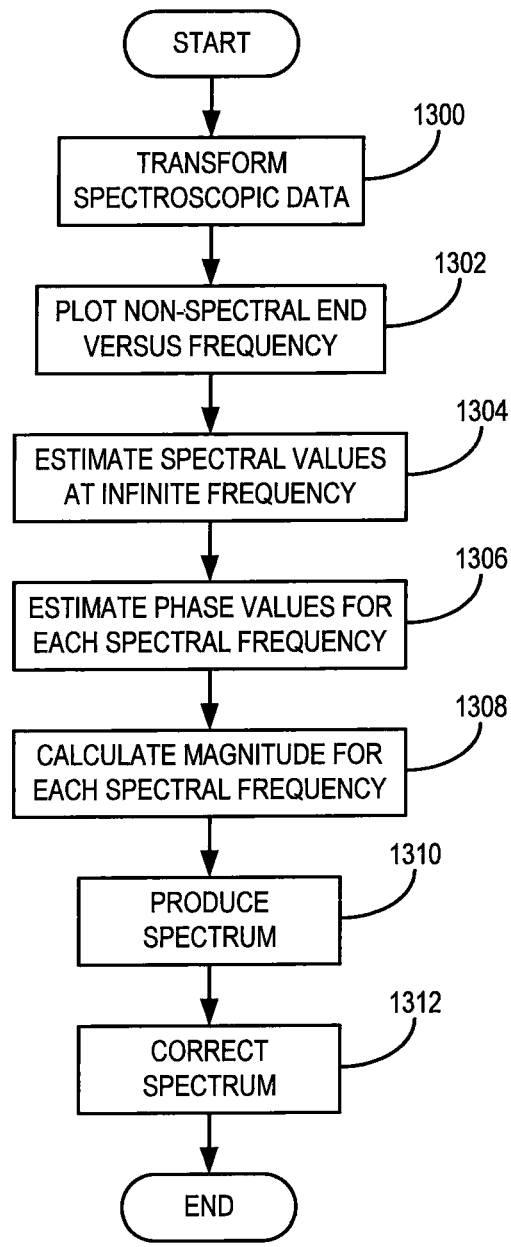
FIG. 13 is a flowchart setting forth the steps of a method for correcting a spectrum, using the MR system of FIG. 10, in accordance with another embodiment of the present invention.

Referring particularly to FIG. 13, an alternative method for correcting the spectroscopic data for phase errors begins by transforming the acquired spectroscopic data, as indicated at step 1300. As discusses above, the Fourier transform of a spectroscopic data set includes one end that has peaks corresponding to the desired spectral information, while the other end, the so-called "non-spectral end", does not. This non-spectral end can be thought of as a baseline curve with a spectrum of zero magnitude superimposed. Thus, the values of the spectra at various frequencies in the non-spectral end correspond to a mirror image of frequencies on the spectral end; however, the non-spectral end includes spectrum values of zero. As a result, the non-spectral end can be employed to produce the spectrum reference line by plotting the spectrum values versus:

$$\alpha, \frac{\alpha}{2}, \frac{\alpha}{3}, \dots, \frac{\alpha}{n},$$

where $\alpha$ is the distance scale factor, or reciprocal frequency, as indicated at step 1302. The spectrum reference line is subsequently derived by fitting the plot of the non-spectral end data versus reciprocal frequency. Here the real and imaginary parts are fitted separately; however, they could be fitted simultaneously as well. As indicated at step 1304, the spectral values at the infinite frequency point are estimated after fitting the non-spectral end data. This is a result of the fitting process as the zero intercept of the fitted data is the extrapolation of the spectral data to the hypothetical infinite frequency. As described above, this hypothetical infinite frequency corresponds to a reciprocal frequency point called the zero point. This zero point is indicative of the offset of a VOI from the isocenter of an MR system.

Each point on the spectrum reference line fitted in step 1302 is shifted to the origin of the complex plane to correct for phase errors, as indicated at step 1306. The magnitude of the spectrum at a given spectral frequency is subsequently calculated at step 1308. As mentioned above, the center of a circle structure corresponds to the point on the fitted spectrum reference line corresponding to the reciprocal frequency. These points are located along the fitted line at:

$$(0+0i)+\alpha \cdot u,$$

Where $(0+0i)$ is a complex zero, $\alpha$ is a distance scale factor, and u is a unit vector that lies along the fitted line. The distance, and therefore the magnitude, is just the length of the vector resulting from subtracting the point on the line from the spectral data point. In the alternative, the distance scale factor can be incorporated into the fitting process performed in step 1302. After calculating the magnitude of the spectrum at the respective spectral frequencies, a complete spectrum is produced at step 1310. Finally, as indicated in step 1312, the amplitudes of the produced spectrum are adjusted in accordance with the calculated $T_2$ decay and zero time, as described above in detail.

Alternative Method for General Corrections

Figure 14:
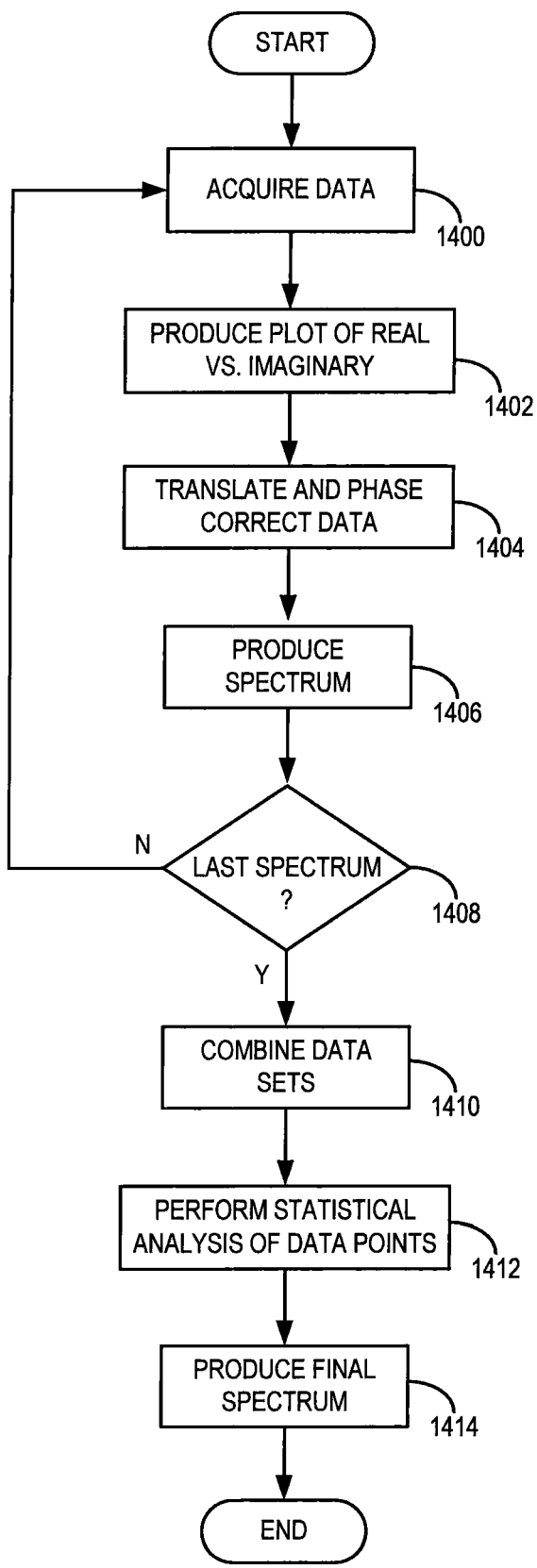
FIG. 14 is a flowchart setting forth the steps of a method for correcting and combining MR spectroscopic data, using the MR system of FIG. 10, in accordance with another embodiment of the present invention.
Figure 15A:
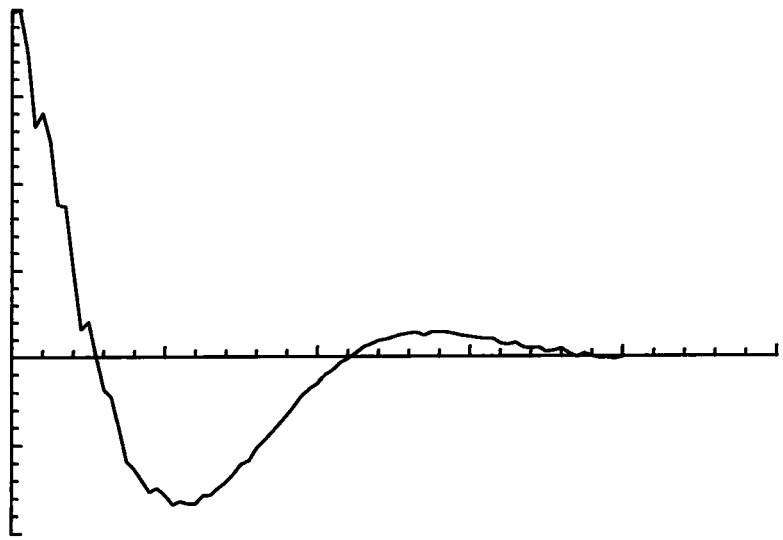
FIG. 15A is a plot of the real part of an exemplary spectroscopic data set acquired with the MR system of FIG. 10.
Figure 15B:
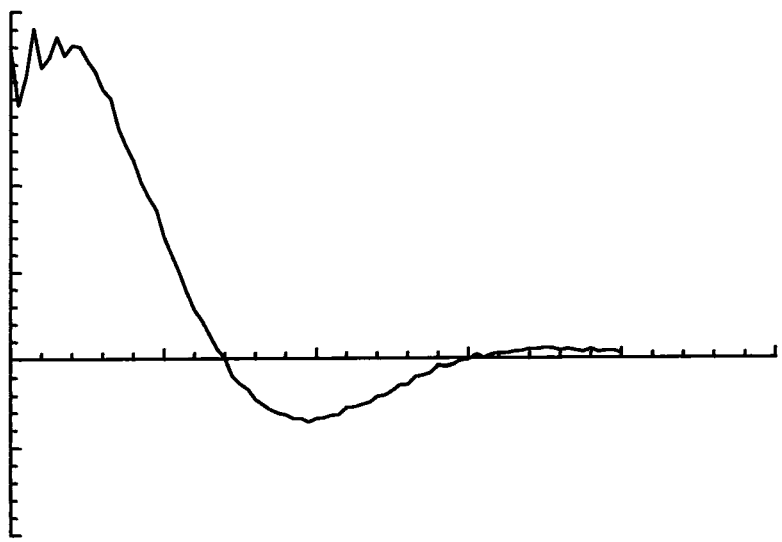
FIG. 15B is a plot of the imaginary part of an exemplary spectroscopic data set acquired with the MR system of FIG. 10.

Referring now to FIG. 14, a process for correcting for phase offsets and time delays in spectroscopic data in accordance with the present invention begins with the acquisition of spectroscopic data using the above-described system, as indicated at step 1400. In the alternative, spectroscopic data can be acquired with other MR spectroscopic devices. Once a data set has been acquired at step 1400, a graph of real versus imaginary data is created at process block 1402. In the case of MR spectroscopy, the signal measured by the MR system is generally the product of a sum of sinusoidal functions and an exponential function. An important part of processing the data is to remove the effects of the exponential function, which is indicative of the $T_2$ decay of the measured signal. The acquired spectroscopic data can be represented by its "real" and "imaginary" components. In general, the real part of the spectroscopic data corresponds to the magnitude of the measured signal and the imaginary part corresponds to the phase of the measured signal. FIGS. 15A and 15B are graphs of the real and imaginary parts of an example spectroscopic data set.

As discussed above, traditionally, a spectroscopic data set is processed with a Fourier transform to convert the time domain data included therein to frequencies and amplitudes in the frequency domain. This Fourier transformed spectroscopic data, or spectrum, can also be represented by its real and imaginary parts in the frequency domain. For example, FIGS. 16A and 16B are graphs of the spectra produced by Fourier transforming the exemplary spectroscopic data of FIGS. 15A and 15B.

Figure 16A:
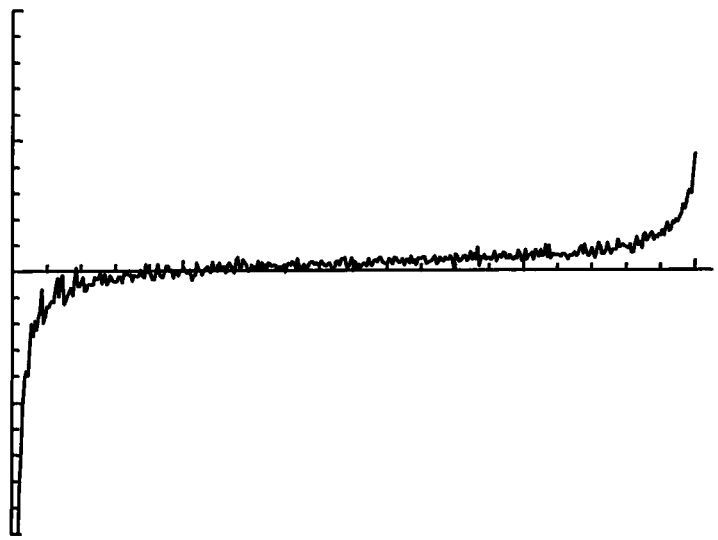
FIG. 16A is a plot of the Fourier transform of the real part of the exemplary spectroscopic data illustrated in FIG. 15A.
Figure 16B:
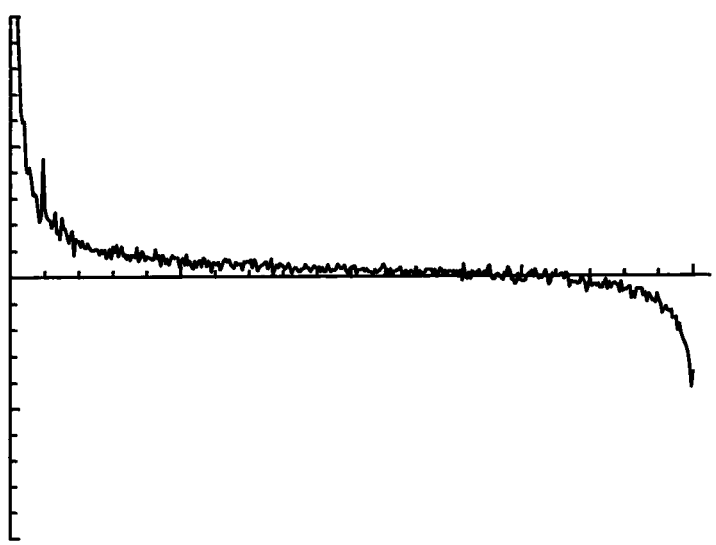
FIG. 16B is a plot of the Fourier transform of the imaginary part of the exemplary spectroscopic data illustrated in FIG. 15B.

Continuing with respect to FIGS. 16A and 16B, it can be seen that the real and imaginary spectra are substantially anti-symmetric. This anti-symmetric form is a result of the exponential decay of the original spectroscopic data. As a result of this anti-symmetric property, the classic approach to eliminating the effects of the signal decay factor is to reverse the data and add it back to itself. It should be noted that there are more spectral peaks at the beginning of the spectra than at their respective ends. It is one goal of the present invention to isolate the information in these spectral peaks while eliminating systematic trends and minimizing noise.

Figure 17A:
FIG. 17A is a plot of the Fourier transform illustrated in FIG. 16A superimposed on a plot of the reverse of the Fourier transform illustrated in FIG. 16A.
Figure 17B:
FIG. 17B is a plot of the difference between the Fourier transform and its reverse illustrated in FIG. 17A.
Figure 17C:
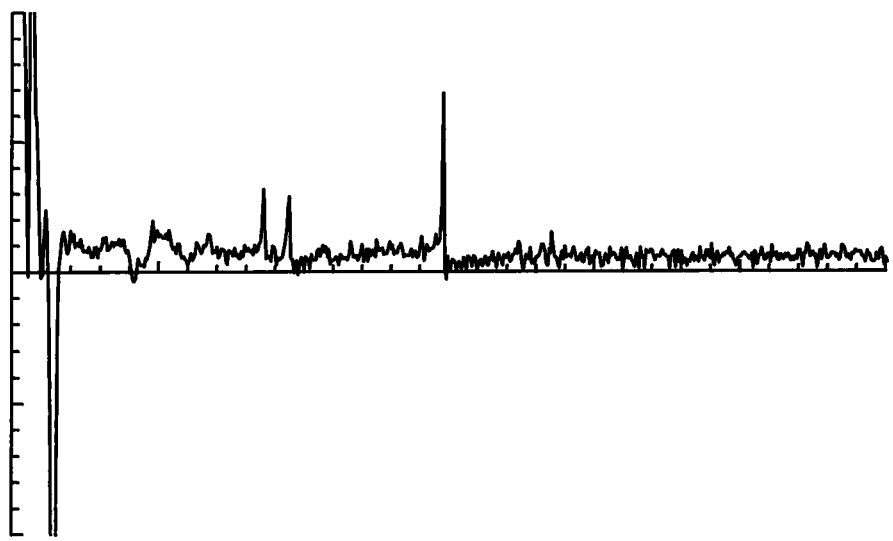
FIG. 17C is a plot of the first 600 data points of the plot illustrated in FIG. 17B.

Referring now to FIG. 17A, the real part (solid line) and the reverse of the real part (dotted line) are superimposed on the same graph of frequency versus amplitude. As illustrated in FIG. 17B, the mirrored curves can be summed to reduce the influence of the substantially exponential term, leaving the desired information. The desired information is the amplitude and frequency of the radio waves that were originally emitted. This point is further illustrated in FIG. 17C, which is a graph of the same data shown in FIG. 17B focused along the frequencies from 0 to 400.

Figure 18A:
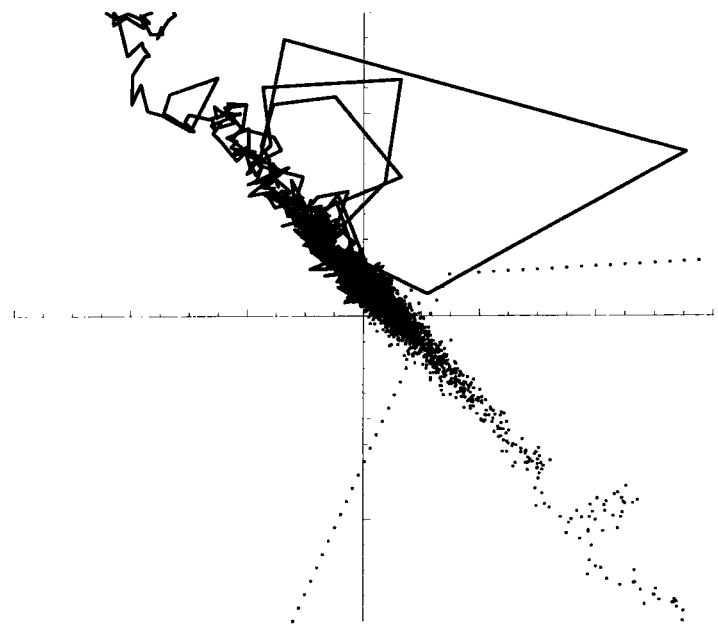
FIG. 18A is a plot of the real part of the exemplary spectroscopic data set illustrated in FIG. 15A versus the imaginary part of the exemplary spectroscopic data set illustrated in FIG. 15B.

Instead of plotting the data as real part versus frequency, as illustrated by, for example, FIG. 17A, the real part can be plotted versus the imaginary part, such as is illustrated in FIG. 18A. Previously, when the real part of the data was added to the reversed real part, it was equivalent to adding the dotted data points to the solid data points in FIG. 18A. However, as is clear in FIG. 18A, the center of the data is not at the origin. Also there are some points that look to be "off the line" of the rest of the data points. These "off the line" points are the important information in the data. Furthermore, the dotted and solid parts of the data are similar, but not exactly identical. This is due to noise superimposed on the theoretically ideal form of the curve. At this point, if the dotted and solid data points are added, the curve illustrated in FIG. 17B would result.

Figure 18B:
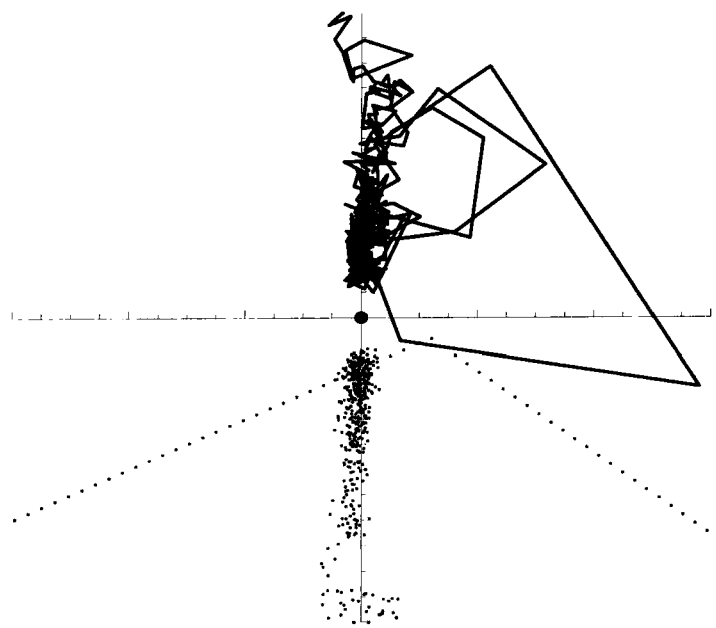
FIG. 18B illustrates the plot of FIG. 18A after corrective translation and rotation of the plotted data.

However, referring back to FIG. 14, the data curve can be translated at step 1404 so that the center of the curve is at the origin, such as illustrated in FIG. 18B. In doing so, there may be some points that are more optimal candidates for the "center of the curve" for some applications and others that are more optimal for other situations. For example, is some cases it may be desirable to select the center of mass, whereas in other cases it may be desirable to select the point with index that is in the center of the data set or the center of mass of a certain subset set of the points.

In the example data shown in FIG. 18B, the data has been translated and rotated (phase shifted). The dotted and solid data now represent the first 600 points in the data set, which are the points that contain the desired spectral information. Again, the dotted and solid points could be added. While the resulting curve similar to the one found before, now the curve would have a baseline at zero, instead of above zero. More importantly, it is no longer necessary to add noisy data to noisy data in order to remove the nearly-exponential decay. Rather, the linear regression line about the y-axis represents a nearly ideal approximation to the curve to be added and zero can be added to the data to get the desired spectrum.

Therefore, referring again to FIG. 14, a spectrum can be produced at step 1406. This process repeats at decision block 1408 until all desired data is acquired. As described above, when acquiring spectroscopic data, phase changes and time shifts are included in data sets. Because of these phase shifts and time shifts, the data do not simply add together in a coherent manner. There can be phase cancellations and interferences. Since the sum of the data is not exact, more noise can be introduced as this summed data set is analyzed as if it were a single data set using the usual methods of simply adding data sets.

Instead of adding the data sets before processing, the data sets are each processed to identify the phase and time shifts, correct the data sets for these variations, and then the data sets are added together at step 1410. By processing each data as outlined above, each converted data set has the same mean value and phase shift along the y-axis. Also, it is contemplated that the Fourier frequency domain data can be averaged directly. Otherwise, the data sets can be returned to the usual time domain by applying Inverse Fourier transform of the data sets. These time domain data can be averaged. This coherent data set can then be analyzed as described above.

Once the phase shifts/offsets and time delays are known, the present invention includes a variety of options for combining the data samples to yield data with less noise and/or higher resolution than the initial data samples. Once the data sets are combined at step 1410, statistical analysis is performed on the data points at step 1412 to determined undesirable points. That is, as described above, when data is obtained with a time delay and phase error, the desired signal information lies along a different trajectory in frequency-phase space than it would be if the signal was detected starting at time zero. The result of this is that the tails of the data curves follow a different path than they would if there was no time delay.

Referring again to FIG. 14, the data can be further processed at step 1412 by either adding or subtracting data points from the reversed data points. That is, the data can be processed to add the dotted points to the solid points or subtracting the dotted from the solid, which results in the production of a final spectrum, as indicated at step 1414.

Depending on the situation, the spectra can be made from the original real and imaginary parts of the Fourier transform data after translating and phase shifting. In the alternative, this data can be added or subtracted from its reverse data for sum or difference data. Spectra can be produced from this data as well. After producing the spectra from individual data sets, the sets can be combined as described above.

The radii of the circle structures correspond to the magnitude information of the spectrum. On the other hand, the phase information of the spectrum is derived from the phase of the points of the circle structures relative to the center of the circle structure. For example, a plot of each point in a circle structure produced from an original spectroscopic data set includes points form a helix around a center line. The angle from the center line to each point in the circle structure is indicative of the corresponding phase information.

It was shown that the useful information lies along a line in frequency versus phase space. Therefore, if a peak in the graph has a frequency and phase that does not correspond to this line, it likely contains noise. After sufficient statistical consideration, points can be eliminated from the graph that are inconsistent with information, or the noise component can be reduced.

A variety of tests can be employed to determine whether a data point should be included or excluded. For example, since all data should lie along the proper frequency-phase line, if a point does not, it is likely noise. Furthermore, in the individual data sets, the information should also lie along the proper line. If one of the sets has data peak that is inconsistent with information, the point can be eliminated from all sets.

Also, the standard deviation of the data points of all data sets should be small if they are information points (since they all should lie along the line). If the standard deviation is too large, the data point can be considered to be noise.

Another Alternative Method for General Corrections

Yet another embodiment of the present invention determines corrections for time delays and phase offsets by first determining initial values for the time delay and phase offset correction parameters from a spectrum produced from an averaged spectroscopic data set. These initial values are subsequently employed to determine correction parameters for each individual spectroscopic data set. Two sets of correction factors are produced to correct for errors represented in the time domain, spectroscopic data. First, separation correction factors are determined, which correct for errors arising from the physical separation between a volume of interest and the MR detector system. Second, temporal correction factors are determined, which correct for errors arising from time delays between the emission and detection of MR signals as well as phase offsets accrued during data acquisition.

Figure 19:
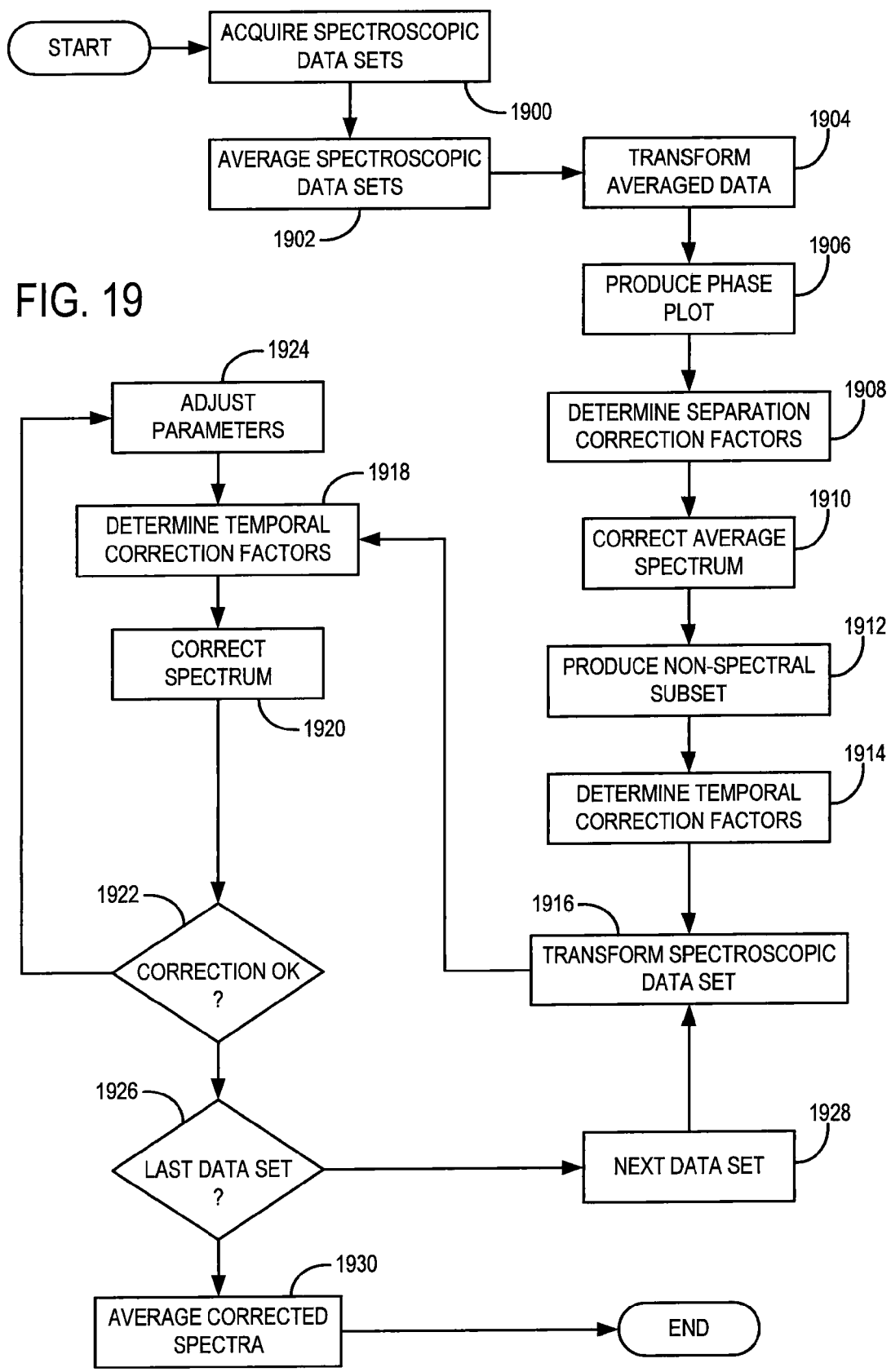
FIG. 19 is a flowchart setting forth the steps of another method of the present invention.
Figure 20:
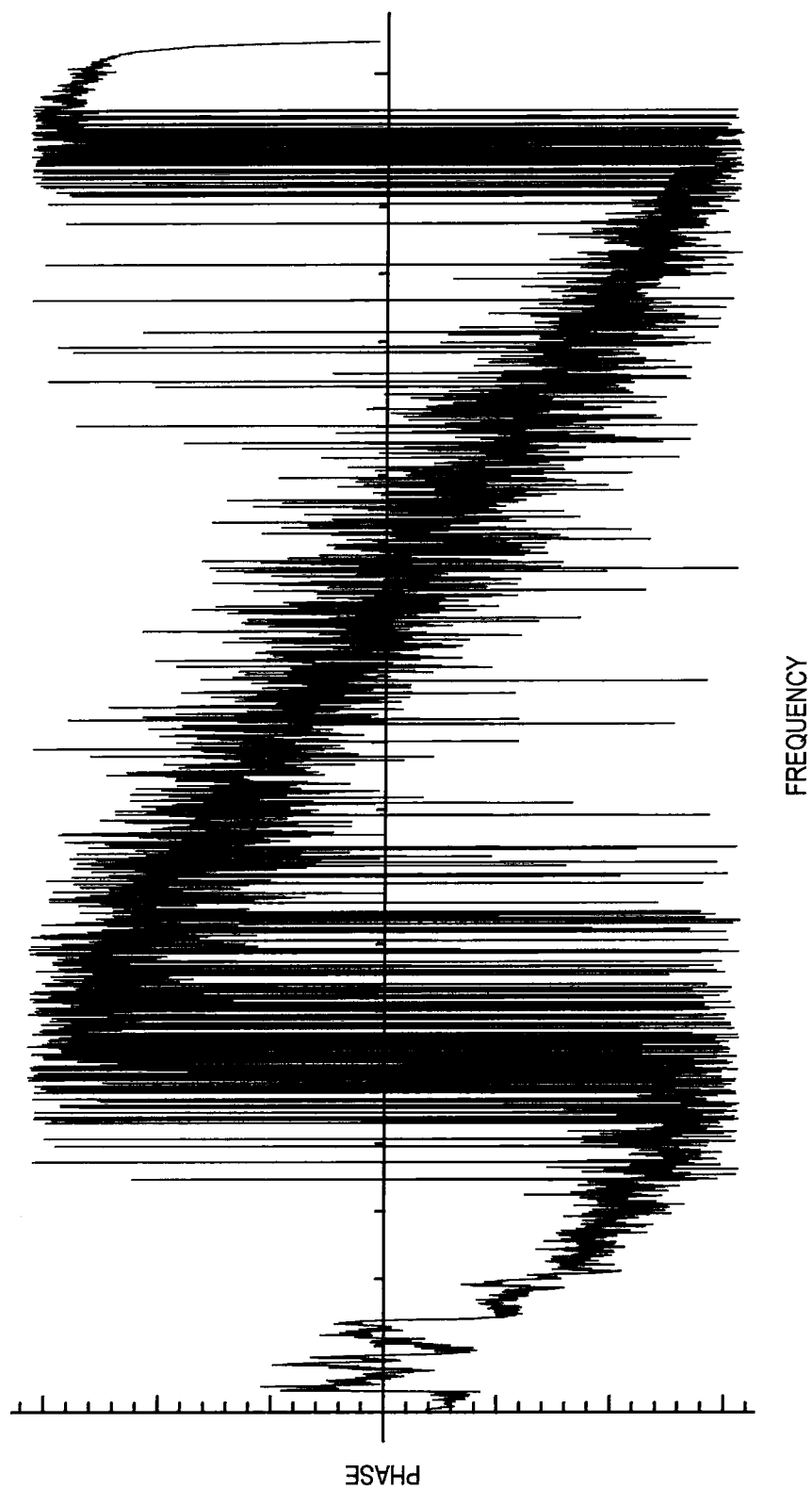
FIG. 20 is a phase plot produced in accordance with the embodiment of the present invention of FIG. 19.

Referring particularly now to FIG. 19, the aforementioned embodiment beings by acquiring a plurality of spectroscopic data sets from a volume of interest (VOI) in a subject, as indicated at step 1900. An average spectroscopic data set is subsequently produced by averaging together all of the acquired spectroscopic data sets, as shown at step 1902. From this average data set, a spectrum is produced at step 1904. This average spectrum is utilized not only to determine initial values for the correction parameters to be applied to each individual data set, but also to determine a correction corresponding to the physical separation between the VOI and the MR detector system. When a plot of the phase values for each data point in the average spectrum versus the corresponding spectral frequency, referred to herein as a "phase plot", is produced, errors arising from the physical separation between the VOI and MR detector system manifest as aliasing. An exemplary plot of such is illustrated in FIG. 20. This aliasing, and the corresponding separation related errors, can be corrected by adjusting the slope of this plot. Therefore, a phase plot is produced from the average spectrum so that errors arising from the separation between the VOI and MR detector system can be corrected, as indicated at step 1906.

Subsequent to the production of the phase plot, correction factors indicative of the detector separation are determined and the slope of the phase plot adjusted, as indicated at step 1908. To determine the correction factors, the desired slope without aliasing is first estimated. One manner in which the slope can be estimated is to calculate the slope corresponding to a line beginning at the point $(f_1, \phi_{max})$ and ending at the point $(f_N, \phi_{min})$ where $f_1$ is the first frequency in the spectrum, $f_N$ is the last frequency in the spectrum, $\phi_{max}$ is the maximum phase value, and $\phi_{min}$ is the minimum phase value. The slope of the aliased phase plot is then set to zero by applying the appropriate slope shift parameters, which have the form:

$$e^{-i\left(arctan\left[\frac{2\pi}{N-1}\right](f-1)+\pi\right)},$$

where f is the spectral frequency and N is the total number of data points in the spectrum. The estimated slope value is now used as an initial value in a non-linear regression method to determine the separation correction factors that, when applied to the average spectrum, shift the slope of the phase plot to the desired value. The zero-sloped phase plot is then adjusted to the desired slope by applying the determined separation correction factors, which also have the form:

$$e^{-i\left(arctan\left[\frac{2\pi}{N-1}\right](f-1)+\pi\right)}.$$

As noted above, a separation correction factor is calculated for each spectral frequency, f. The average spectrum is subsequently corrected using the calculated correction factors by multiplying each data point in the average spectrum by the corresponding correction factor, as indicated at step 1910.

Figure 21:
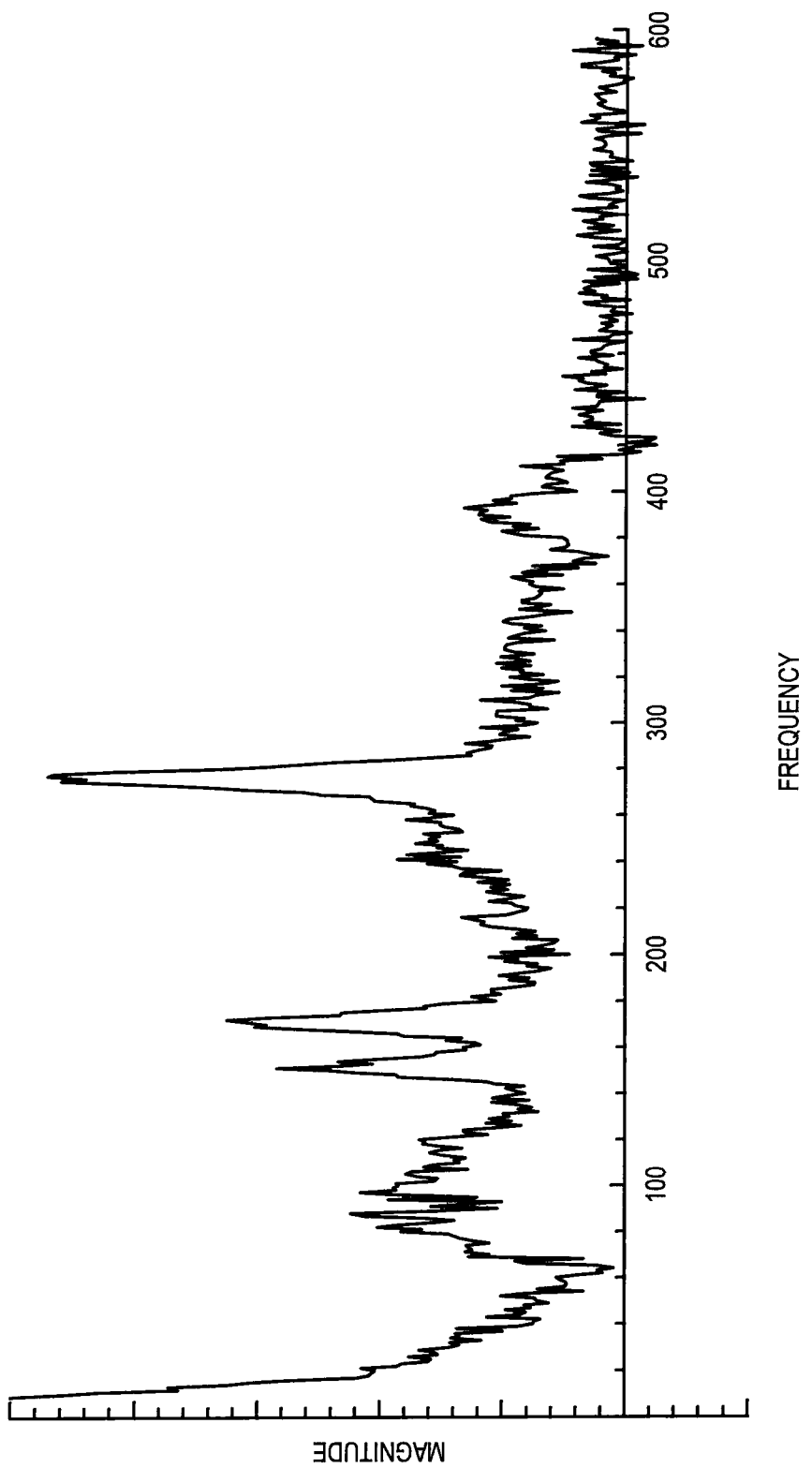
FIG. 21 is a plot of an exemplary spectrum produced from acquired spectroscopic data.

After the separation correction factors have been calculated, a selected subset of spectral frequencies is determined, from which temporal correction factors will be calculated, as indicated at step 1912. This subset is utilized not only for analyses performed on the average spectrum, but also on individual spectra, as will be discussed in detail below. The frequency subset is selected using knowledge of the desired chemical species, from which the spectrum is produced. In general, the selected frequency subset begins at some spectral frequency value after the last value containing spectral information indicative of the desired chemical species. Consider, for example, an acquired spectroscopic data set that includes 4096 time points. The corresponding spectrum produced from such a data set includes 4096 data points corresponding to 4096 spectral frequencies; however, not all of these data points contain spectral information. In the exemplary spectrum shown in FIG. 21, for example, the desired chemical species has a last peak around the spectral frequency f=390. Using this example, the frequency subset would begin at a frequency value after f=390, such as, for example f=600. One choice of end point of the frequency subset is the midpoint of the spectrum. Using the above example again, this would correspond to a value of f=2048. It should be appreciated by those skilled in the art that many alternative selection criteria of a frequency subset are possible, and such selections will differ depending on the desired chemical species and the application at hand.

Temporal correction values are subsequently calculated using the data points from the average spectrum that are included in the frequency subset, as indicated at step 1914. A non-linear regression method is performed on the data points included in the selected subset of the spectrum. Exemplary non-linear regression methods that can be employed include a sum of squares of the real part of the data points included in the frequency subset. In the alternative, the area under real part of the portion of the spectrum containing spectral information can be minimized. The result of performing the non-linear regression is the calculation of temporal correction terms having the following the form:

$$e^{i(A \cdot f + B)},$$

where A is a frequency constant, f is the spectral frequency, and B is a phase constant. The temporal correction factors determined from the average spectrum are stored and later utilized as initial values for calculating temporal correction factors for each individual spectra produced from the originally acquired spectroscopic data sets.

Therefore, a spectroscopic data set is first selected and transformed to produce an individual spectrum, as indicated at step 1916. Subsequently, temporal correction factors for this individual spectrum are calculated at step 1918. This method proceeds in similar fashion to the method carried out using the average spectrum. For example, the same frequency subset is employed, over which a non-linear regression is performed to determine a series of temporal correction factors. When performing the non-linear regression this time, however, the temporal correction factors calculated from the average spectrum are employed as initial values to reduce the computational burden of the process. The individual spectrum is then corrected by multiplying each data point in the spectrum by the temporal correction factor corresponding to the respective spectral frequency, as indicated at step 1920.

Figure 22A:
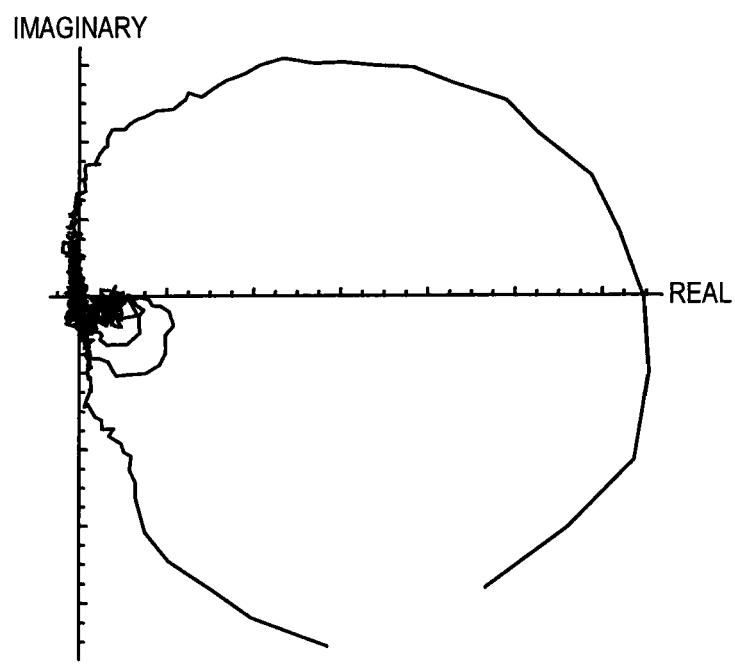
FIG. 22A is a polar plot indicative of the real and imaginary parts of a spectrum that has been corrected in accordance with the embodiment of the present invention of FIG. 19.
Figure 22B:
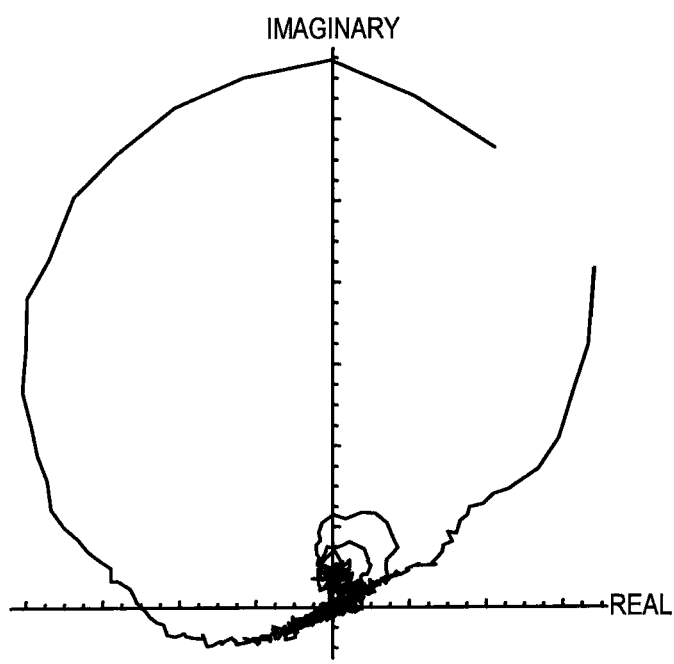
FIG. 22B is a polar plot indicative of the real and imaginary parts of a spectrum that has not been corrected for errors resulting from phase and time shifts in the corresponding acquired spectroscopic data.

A check is made as to whether the correction applied to the spectrum is satisfactory at decision block 1922. This check is achieved by producing a polar plot of the real and imaginary parts of the spectrum in the real-imaginary plane. If the polar plot is substantially aligned along real-axis, then correction is satisfactory and the method proceeds. An exemplary polar plot of a satisfactorily corrected spectrum is illustrated in FIG. 22A. A well time corrected spectrum is demonstrated when the polar plot looks like circles that are all tangent to each other at the origin with their farthest points from the origin all aligned. If this alignment is not along the real axis, it can be readily shifted to be along the axis by a phase change. On the other hand, if the furthest points on the circles represented in the polar plot are not substantially aligned, then the parameters of the non-linear regression are adjusted at step 1924 and an updated non-linear regression is performed to calculate a new set of temporal correction factors. An exemplary polar plot of a non-satisfactorily corrected spectrum is illustrated in FIG. 22B. Note also that FIGS. 18A and 18B are similar in construction to FIGS. 22A and 22B when viewed along the long axis of the data points.

Exemplary polar plots are in three dimensions having coordinate axes corresponding to frequency, the real part of the spectrum, and the imaginary part of the spectrum. The data points are connected by a smooth line in three-dimensional space by an interpolation function, such as, for example, cubic spline. Such a line looks like a helix in space with one side having each loop of the helix intersect a line.

After the individual spectrum is satisfactorily corrected, a determination is made whether all of the individual spectra have been corrected, as indicated at decision block 1926. If not, the next spectroscopic data set is selected at step 1928 and the above-described method is repeated. Once all of the individual spectra have been produced and corrected, an average spectrum is produced at step 1930. As described above, this average spectrum exhibits an increase in signal-to-noise ratio and, as a result of correcting the individual spectra contributing to the average, the coherent addition of the plurality of individual spectra is more accurate. The smooth, nearly circular helix structure produced as described-above is easily interpolated for fitting to so-called "Gold Standard" spectra in order to quantify the chemical species in the spectrum. This is contrary to attempting to fit a "Gold Standard" spectrum to the jagged real or imaginary spectra directly. The fitting is done by a non-linear regression or minimization method.

As discussed above, in one embodiment of the present invention, a method for producing a spectrum with a magnetic resonance imaging (MRI) system includes acquiring a spectroscopic data set and producing, from the acquired spectroscopic data set, a plurality of time-shifted spectroscopic data sets. The step of producing these time-shifted spectroscopic data sets may include, for example, producing a first and second time-shifted spectroscopic data set. More specifically, a first time-shifted spectroscopic data set is produced by removing the first data point in the originally acquired spectroscopic data set and appending a complex zero to the end of the data set. A second time-shifted spectroscopic data set is thus produced by removing the first data point in the first time-shifted spectroscopic data set and appending a complex zero to the end of the first time-shifted spectroscopic data set.

Subsequently, a spectrum is produced by transforming the acquired spectroscopic data set and, likewise, a plurality of time-shifted spectra are produced by transforming the time-shifted spectroscopic data sets. Using both the spectrum and time-shifted spectra, the spectroscopic data set is corrected for errors arising from time and phase shifts. A corrected spectrum is subsequently produced by transforming the corrected spectroscopic data.

The correction of the spectroscopic data set may include, for example, calculating a zero time from the acquired spectroscopic data set and the time-shifted spectroscopic data sets. The correction may also include, for example, calculating a plurality of phase offsets from the spectrum and the time-shifted spectra. Such phase offsets are calculated, for example, by producing a plurality of difference spectra, wherein each difference spectrum is produced by subtracting two time-shifted spectra. In this manner, the zero time is determined using the produced difference spectra. In particular, a slope value for each difference spectra is calculated using a regression method and a phase difference line is subsequently produced using the calculated slope values. In the alternative, the phase offsets may be calculated by producing a plurality of circle structures using the spectrum and the time-shifted spectra, wherein one circle structure is produced for each spectral frequency represented in the spectrum.

Figure 23A:
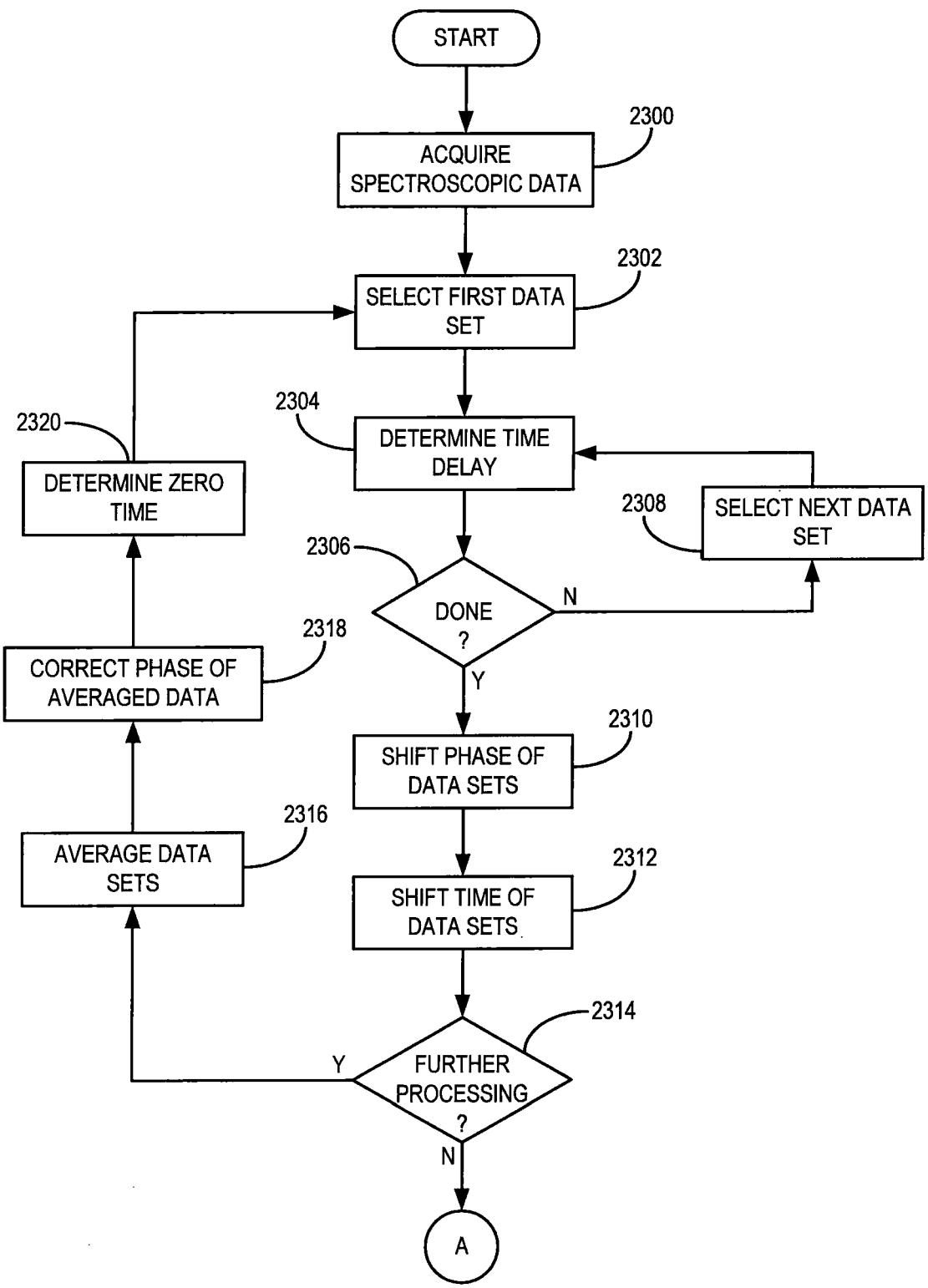
FIGS. 23A and 23B illustrate a flowchart setting forth the steps of an exemplary method for producing a corrected spectrum with significantly reduced noise levels, using the MR system of FIG. 10, in accordance with one embodiment of the present invention.
Figure 23B:
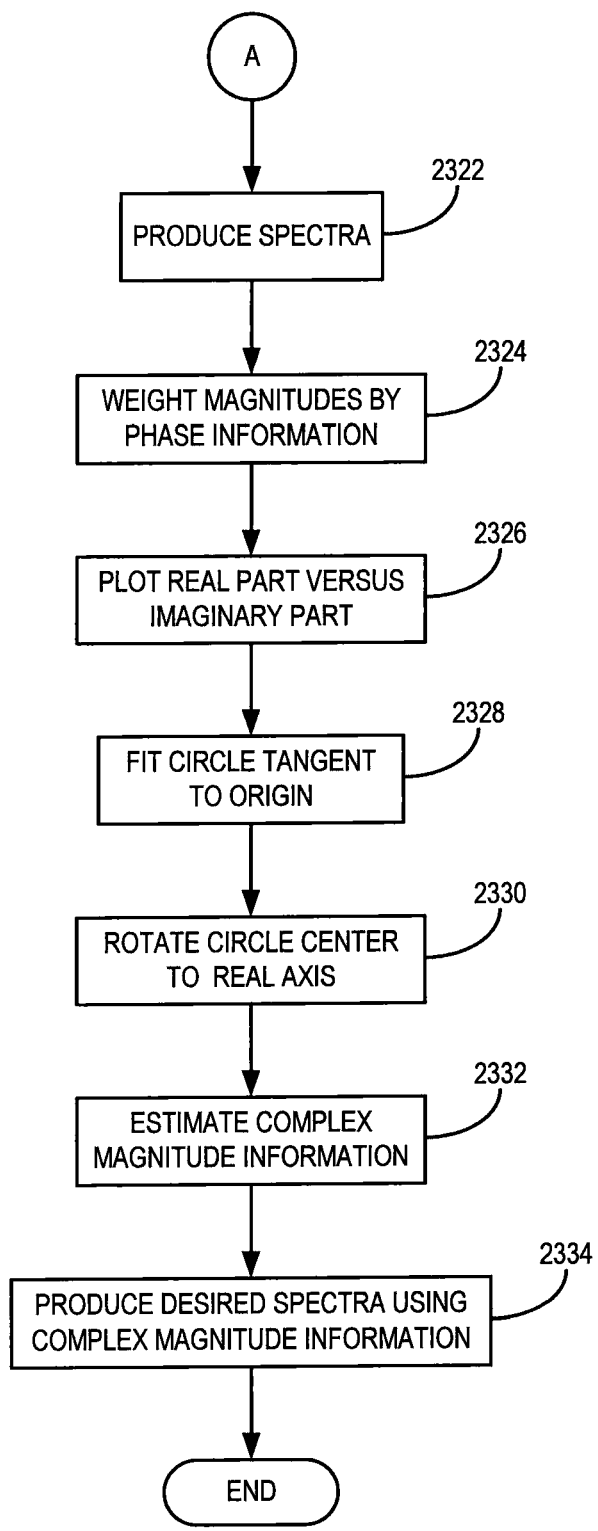

Referring particularly to FIGS. 23A and 23B, a flowchart setting forth the steps of an exemplary method for producing a corrected spectrum is illustrated. The method begins by acquiring spectroscopic data with an MR system, as indicated in step 2300. For example, the spectroscopic data is acquired by sampling free induction decays (FIDs); however, in general, the spectroscopic data is acquired with any number of methods known to those skilled in the art. For example, when acquiring spectroscopic imaging data from a subject in an MRI system, a chemical shift imaging (CSI) pulse sequence can be employed to acquire the requisite data. As described above, the spectroscopic data includes information indicative of radiofrequency signals emitted from a volume-of-interest (VOI) in a subject. The first few data points acquired with the MR system are sometimes not accurate, thus the MR system might need to acquire approximately ten data points before it reaches a reliable equilibrium steady state for data acquisition.

A first spectroscopic data set is selected for processing, as indicated at step 2302. As indicated at step 2304, this processing includes first calculating the phase of the spectroscopic data set, and then fitting that phase to a linear function in order to determine a time delay that occurred between excitation of the VOI and detection of the NMR signals therefrom. A determination is made at decision block 2306 whether all of the desired data sets have been analyzed. If not, a next spectroscopic data set is selected at step 2308, and step 2304 is repeated. Once all of the desired data sets have had their associated time delay determined, further processing of the data sets commences.

For each spectroscopic data set, the associated fitted linear function is utilized to shift the phase of the data points in the data set so that the points lie along a positive real axis, as indicated at step 2310. The data set with the shortest associated time delay is then compared with each other data set. Each data set is interpolated in time and shifted along the time axis until each best coincides with the points of the data set identified as having the shortest time delay, as indicated at step 2312.

Optionally, the processed spectroscopic data sets are averaged together, as determined at decision block 2314 and indicated at step 2316. The phase information of this averaged data set is fitted to a linear function and this function is used to correct the phase data to have a slope and intercept of zero, as indicated at step 2318. This slope is due to the fact that the time delay of the first data set is not actually zero. The slope of the linear function is calculated and multiplied by $(n-1)2\pi$, where n is the number of data points in the averaged data set, to determine the actual zero time, as indicated at step 2320. The processing in steps 2302-2312 is then repeated with the proper time zero in order to produce more accurate spectra. In such an instance, the delay time $\delta t_n$ is replaced by $\delta t_n + \delta t_0$, where $\delta t_0$ is the time delay of the first data set acquired, as measured from the actual zero time.

The time domain spectroscopic data sets are subsequently Fourier transformed into the frequency domain, as indicated at step 2322. By way of example, this transformation is performed using the so-called manual form of the Fourier transform rather than the functional form because using the manual form allows the incorporation of the time delay into the transformation. An exemplary manual Fourier transform is given by:

$$\sum_{t=0}^{4095} z_n(t+1) \cdot e^{i\left(\frac{2\pi}{4095} \cdot (t-\delta t_n) \cdot \alpha\right)}$$

where $z_n(t+1)$ is the data point of the $n^{th}$ spectroscopic data set at time point $(t+1)$; $\delta t_n$ is the time delay calculated in step 2304 for the $n^{th}$ spectroscopic data set; and $\alpha$ is a resolution factor that can be varied to produce spectra of different spectral resolutions. The inclusion of the time delay into the Fourier transform allows the data sets to be effectively coregistered. To produce high resolution spectra, the resolution factor is selected to be less than one. In general, a resolution factor of $\alpha = 1/N$ will result in a spectrum having an N-fold increase in its spectral resolution. This added resolution, however, reduces the signal-to-noise ratio (SNR) in the produced spectrum. It is a teaching of the invention, however, that an appropriate balance between increased resolution and decreased SNR can be achieved such that an improved spectral resolution can be realized without undue loss of SNR.

The produced spectra are further improved by reducing the noise therein by weighting the magnitude information in the spectra by phase information in the same spectra, as indicated at step 2324. For example, the following weighting is used:

$$\hat{s}(f) = Re(s(f)) \cdot e^{i Im(s(f))},$$

where $\hat{s}(f)$ is the improved spectral data at frequency, f; $Re(s(f))$ is the real part, or magnitude information, for the spectrum at frequency, f; and $Im(s(f))$ is the imaginary part, or phase information, for the spectrum at frequency, f.

Figure 24:
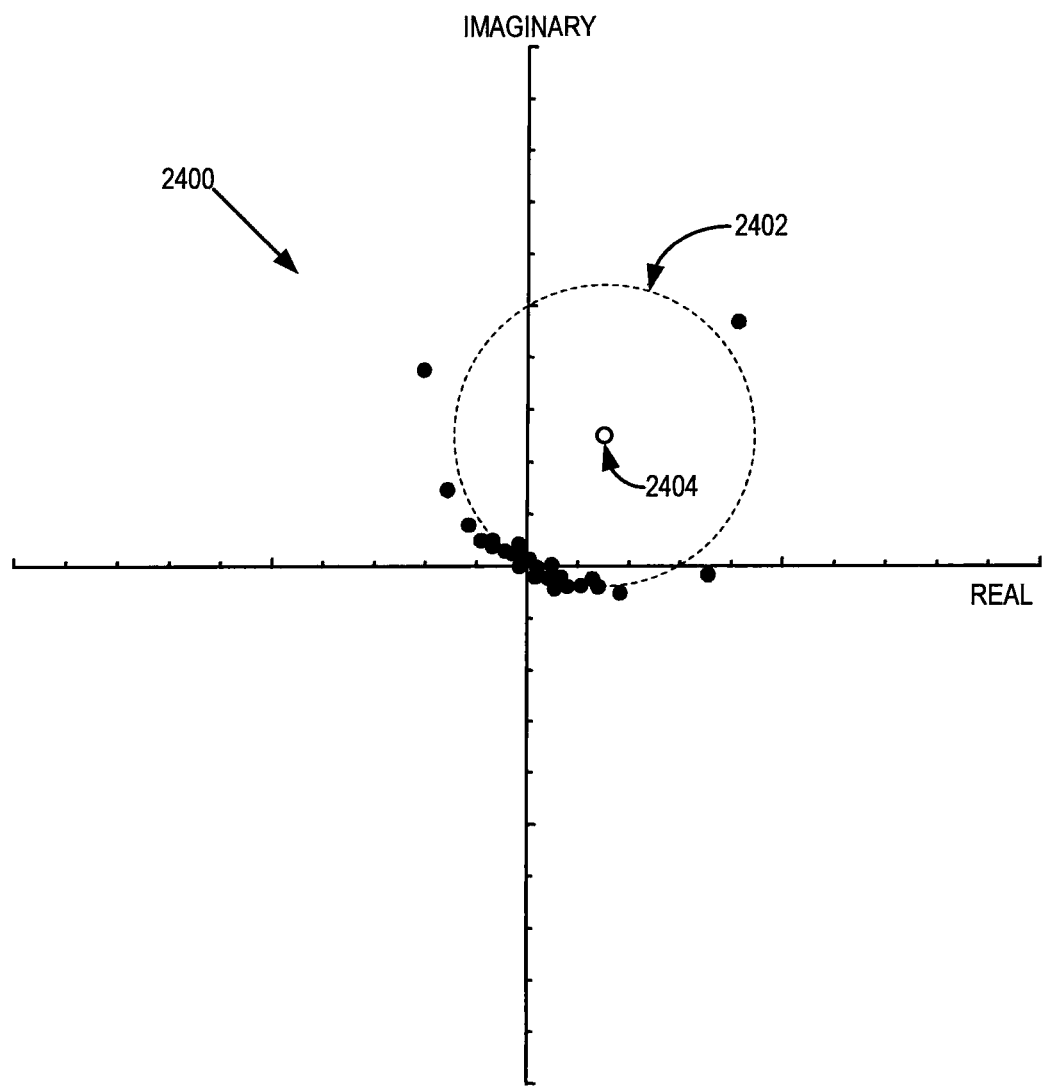
FIG. 24 is a polar plot indicative of the real and imaginary parts of an improved spectrum produced in accordance with the method of FIG. 23.

A plot of the real part of these improved spectra versus the imaginary part of the improved spectra is produced next, as indicated at step 2326. An exemplary such plot 2400 is illustrated in FIG. 24, to which reference is now made in addition to FIGS. 23A and 23B. As indicated at step 2328, a circle 2402 is fit to the produced plot 2400, such that the circle 2402 is tangent to the origin of the real-imaginary plane. The center 2404 of this tangent circle 2402 is then rotated such that the center 2404 lies along the real axis, as indicated at step 2330. In this manner, all of the improved spectra are phase corrected such that their phases are aligned to a phase of zero. Optionally, a high resolution spectrum is produced next, as indicated at step 2332.

Complex magnitude information is then calculated from the spectra, as indicated at step 2334. For each frequency in a given spectrum, the phase of that frequency shifts over time by a fixed amount and at a fixed rate. Since the data points in each shifted, corrected spectroscopic data set are equally spaced, there is a fixed phase shift between each frequency point in the corresponding series of shifted, corrected spectra. This relationship can also be viewed as a temporal variation in the magnitude at a given spectral frequency. Taken from this viewpoint, for each spectral frequency there is a sinusoidal relationship between the magnitude for that spectral frequency and time. This relationship can be seen, for example, in FIGS. 3A-3C, which show exemplary plots of imaginary magnitude versus time for frequencies of f=30 (FIG. 3A), f=95 (FIG. 3B), and f=400 (FIG. 3C). This sinusoidal relationship is exploited, and a trend over time is established from the shifted, corrected spectra to achieve this exploitation. For example, the spectra can be fit to a sinusoidal curve to estimate the real and imaginary magnitudes of the spectra. In the alternative, however, the circle structures method discussed above can be utilized, as can a standard deviation based approach and one that looks to the difference between the maximum and minimum spectral values over time. After the real and imaginary magnitude values for each spectral frequency are determined in this manner, they are combined to form a complex magnitude value for the spectral frequency.

From the corrected spectroscopic data and the complex magnitude information, a desired spectrum indicative of the spin species present in the subject is then produced, as indicated at step 2336. In general, the imaginary part of the complex magnitude information is negligible; therefore, in most instances the desired spectra are produced as the real part of the complex magnitude information.

In the alternative to the foregoing processing steps, the spectroscopic data sets can also be processed as follows. The phase of the complex valued spectroscopic data can be plotted and this phase adjusted so that the plotted data lies along a line from the origin to the time point (n,0) in the data set, where n is the number of time points in the data set. This adjustment is achieved by multiplying the phase information by complex exponential functions. Exemplary complex exponentials include:

$$e^{i(\phi + t \cdot \Delta)};$$

where $\phi$ is the phase at the time point, t, and $\Delta$ is a correction factor. This processing can equivalently be performed in the frequency domain in order to find a time domain correction that will yield the correct frequency domain phase. But that is equivalent to this.

The present invention has been described in terms of one or more preferred embodiments, and it should be appreciated that many equivalents, alternatives, variations, and modifications, aside from those expressly stated, are possible and within the scope of the invention. For example, the present invention may be employed in applications other than MR spectroscopy where it is desirable to produce signals having increased SNR. As it will be appreciated by those skilled in the art, the present invention will find use in applications where data is acquired as signals that are based on the sum of sinusoidal curves, such as those described above. Such applications include traditional nuclear magnetic resonance (NMR), as used in the chemistry laboratory, and applications that utilize sound waves. Exemplary applications involving sound waves include, for example, sonar.

The invention claimed is:

1. A method for producing a spectrum with a magnetic resonance imaging (MRI) system, the steps comprising:
   a) exciting, with the MRI system, a volume of interest;
   b) acquiring, with the MRI system, a spectroscopic data set from the volume of interest;
   c) transforming the spectroscopic data set to produce a spectrum;
   d) determining a correction factor using temporal information from the spectroscopic data set that includes a zero time indicative of a time at which a signal is first emitted from the volume of interest following the excitation in step a) and a time delay between the zero time and a time at which the signal is detected by the MRI system in step b); and
   e) applying the correction factor to the spectrum produced in step c) to correct for errors attributable to phase and time shifts in the spectroscopic data set acquired in step b).

2. The method as recited in claim 1 in which the errors attributable to phase and time shifts in the acquired spectroscopic data set result from at least one of a time delay occurring between steps a) and b), and a location of the volume of interest with respect to the MRI system.

3. The method as recited in claim 1 in which step d) further comprises determining a separation correction using information about a physical separation between the volume of interest and the MRI system.

4. The method as recited in claim 3 in which step e) includes multiplying each data point in the spectrum by the correction factor and the separation correction factor.

5. The method as recited in claim 1 in which steps a)-c) are repeated to produce a plurality of spectroscopic data sets and corresponding spectra.

6. The method as recited in claim 5 in which step d) includes averaging the plurality of spectra to produce an average spectrum.

7. The method as recited in claim 6 in which step d) includes producing a phase plot by plotting a phase of each data point in the average spectrum as a function of frequency.

8. The method as recited in claim 7 in which step d) includes:
   determining the slope of the phase plot;
   estimating a shifted slope; and
   calculating the correction factor that shifts the determined slope to the estimated slope.

9. The method as recited in claim 5 in which step d) includes:
   selecting a subset of frequencies; and
   calculating an initial correction factor by performing a regression on a subset of the average spectrum corresponding to the selected subset of frequencies.

10. The method as recited in claim 9 in which step d) includes calculating a correction factor for each spectrum produced in step c) by performing a regression, using the calculated initial correction factor, on a subset of each spectrum corresponding to the selected subset of frequencies.

11. The method as recited in claim 1 further including:
    f) producing, from the acquired spectroscopic data set, a plurality of time-shifted spectroscopic data sets; and
    g) transforming the plurality of time-shifted spectroscopic data sets to produce a plurality of time-shifted spectra.

12. The method as recited in claim 11 in which step d) includes:
    d)i) calculating a zero time from the spectroscopic data set acquired in step b) and the time-shifted spectroscopic data sets produced in step f); and
    d)ii) calculating a plurality of phase offsets from the spectrum produced in step c) and the time-shifted spectra produced in step g).

13. The method as recited in claim 12 in which step d)i) includes:
    producing a plurality of difference spectra, wherein each difference spectrum is produced by subtracting two time-shifted spectra; and
    determining the zero time using the difference spectra.

14. The method as recited in claim 13 in which step d)i) includes:
    calculating a slope value for each difference spectra using a regression method; and
    producing a phase difference line using the calculated slope values.

15. The method as recited in claim 12 in which step d)ii) includes producing a plurality of circle structures using the spectrum produced in step c) and the time-shifted spectra produced in step g), wherein one circle structure is produced for each spectral frequency represented in the spectrum produced in step c).

16. The method as recited in claim 1 further including:
    f) correcting the spectroscopic data set acquired in step b) with the correction factor determined in step d) in order to produce a corrected spectroscopic data set;
    g) producing, from the corrected spectroscopic data set, a plurality of corrected time-shifted spectroscopic data sets;
    h) transforming the plurality of corrected time-shifted spectroscopic data sets to produce a corresponding plurality of corrected time-shifted spectra; and
    i) producing an improved spectrum using the plurality of corrected time-shifted spectra.

17. The method as recited in claim 16 in which step i) includes estimating a complex magnitude value for each spectral frequency in the corrected time-shifted spectra.

18. The method as recited in claim 17 in which each complex magnitude value is estimated in step i) by fitting each value in the plurality of corrected time-shifted spectra for a given spectral frequency to a sinusoidal curve.

* * * * *